(12) United States Patent
Nilsson et al.

(10) Patent No.: US 7,601,353 B2
(45) Date of Patent: Oct. 13, 2009

(54) PEPTIDE-BASED PASSIVE IMMUNIZATION THERAPY FOR TREATMENT OF ATHEROSCLEROSIS

(75) Inventors: Jan Nilsson, Genarp (SE); Roland Carlsson, Lund (SE); Jenny Bengtsson, Lund (SE); Leif Strandberg, Kävlinge (SE)

(73) Assignee: Forskarpatent I SYD AB, Lund (SE)

( * ) Notice: Subject to any disclaimer, the term of this patent is extended or adjusted under 35 U.S.C. 154(b) by 171 days.

(21) Appl. No.: 11/323,123

(22) Filed: Dec. 30, 2005

(65) Prior Publication Data

US 2007/0098723 A1 May 3, 2007

(51) Int. Cl.
*A61K 39/395* (2006.01)
*C07K 16/00* (2006.01)

(52) U.S. Cl. .............................. 424/142.1; 530/388.15

(58) Field of Classification Search .................. None
See application file for complete search history.

(56) References Cited

U.S. PATENT DOCUMENTS

| 5,494,791 | A | 2/1996 | Cohen |
| 5,861,276 | A | 1/1999 | Kwak et al. |
| 5,972,890 | A | 10/1999 | Lees et al. |
| 6,225,070 | B1 | 5/2001 | Witztum et al. |
| 2007/0098725 | A1* | 5/2007 | Nilsson et al. ........... 424/145.1 |

FOREIGN PATENT DOCUMENTS

| EP | 0433088 B1 | 6/1997 |
| WO | WO9832845 A1 | 7/1998 |
| WO | WO9842751 A1 | 10/1998 |
| WO | WO 99/08109 | * 2/1999 |
| WO | WO9908109 A3 | 2/1999 |
| WO | WO 99/18986 | 4/1999 |
| WO | WO9918986 A1 | 4/1999 |
| WO | WO0132070 A2 | 5/2001 |
| WO | WO0164008 A2 | 9/2001 |
| WO | WO02080954 A1 | 10/2002 |

OTHER PUBLICATIONS

Tinahones et al., Journal of Lipid Research, 2005, 46:452-457.*
Ameli et al., 1996, Arterioscler. Thromb. Vasc. Biol., 16:1074-9.*
Fredrikson et al., 2003, Arterioscler. Thromb. Vasc. Biol., 23(5):879-84.*
Schiopu et al., 2006, Clin. Immunol., 119:S147-8.*
Strom et al., 2007, Atherosclerosis, 190:298-305.*
Borrebaeck and Carlsson (2001) Curr. Opin. Pharmacol., 1:404-8.
Bruce et al. (1999) Int. J. Biochem. Cell Biol., 1409-20.
Caligiuri et al. (2002) J. Clin. Invest., 109:745-753.
Dimayuga et al. (2002) Arterioscl. Thromb. Vasc. Biol., 22:644-9.
Freigang et al. Arterioscl. Thromb. Vasc. Biol. (1998) 1973-82.
George et al. (1998) Atherosclerosis, 138:147-52.
Griffiths et al. (1994) EMBO J., 13:3245-3260.
Hammer et al. (1995) Aterioscl. Thromb. Vasc. Biol., 704-13.
Hoogenboom et al. (1992) J. Mol. Biol., 227:381-8.
Jovinge et al. (1997) Aterioscl. Thromb. Vasc. Biol., 17:2225-31.
Li et al. (2000) Biochemistry, 39 6296-6309.
McCafferty et al. (1990) Nature, 348:552-4.
Merck Manual of Diagnosis and Therapy (1999; 17th ed.) pp. 1656-1657.
Milstein and Kohler (1975) Nature, 256:495-7.
Neuberger et al. (1985) Nature, 314:268-70.
Palinski et al. (1989) Proc. Natl. Acad. Sci. USA, 86:1372-6.
Palinski et al. (1995) Proc. Natl. Acad. Sci. USA, 92:821-5.
Reff et al. (2001) Crit. Rev. Oncol/Hematol. 40:25-35.
Regnstrom et al. Atherosclerosis, 82:43-51.
Soderlind et al. (2000) Nature BioTechnol., 18:851-6.
Soderlind et al. (2001) Comb. Chem & High Throughput Screen, 4:409-16.
Steinberg et al. (1989) New England J. Med., 320:915-924.
Tinahones et al. (2005) J. Lipid Res. 46:452-7.
Valentinova et al. (1994) Biol. Chem., 651-8.
Zhou et al. (1998) J. Clin. Invest.,101:1717-25.
Reff et al., "A review of modifications to recombinant antibodies: attempt to increase efficacy in oncology applications" Oncology Hematology, (2001) pp. 25-35.
The Merck Manual of Diagnosis and Therapy. 17th Edition, published by Merk Research Labratories, 1999, pp. 1654-1659.
Tinahones et al., "Influence of age and sex on levels of anti-oxidized LDL antibodies and anti-LDL immune complexes in the general population" Journal of Lipid Research, vol. 46, 2005, pp. 452-457.
Li et al., "Three-Dimensional Structures of the Free and Antigen-Bound Fab from the Monoclonal Antilysozyme Antibody HyHEL-63" Biochemistry 2000, pp. 6296-6309.

* cited by examiner

*Primary Examiner*—Ilia Ouspenski
(74) *Attorney, Agent, or Firm*—Gauthier & Connors LLP

(57) ABSTRACT

The present invention relates to passive immunization for treating or preventing atherosclerosis using an isolated human antibody directed towards at least one oxidized fragment of apolipoprotein B in the manufacture of a pharmaceutical composition for therapeutical or prophylactical treatment of atherosclerosis by means of passive immunization, as well as method for preparing such antibodies, and a method for treating a mammal, preferably a human using such an antibody to provide for passive immunization.

5 Claims, 20 Drawing Sheets

FIG. 1
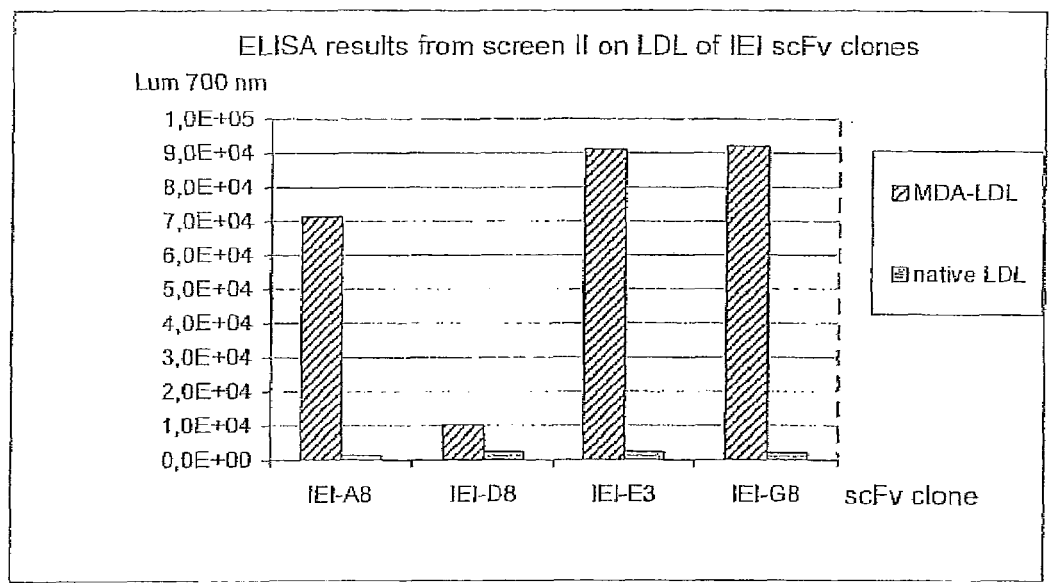
FIG. 1A
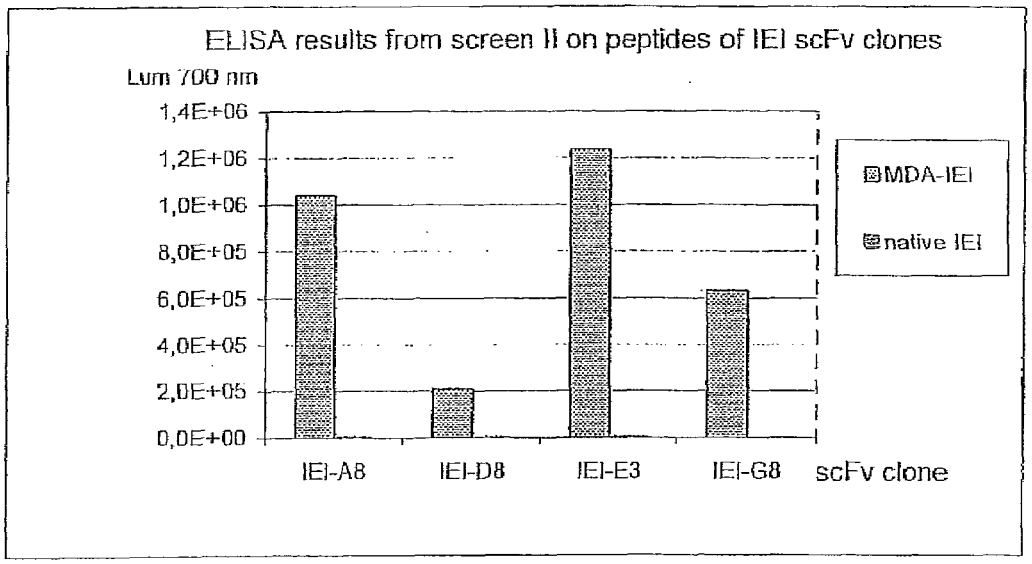
FIG. 1B

FIG. 1 cont'd
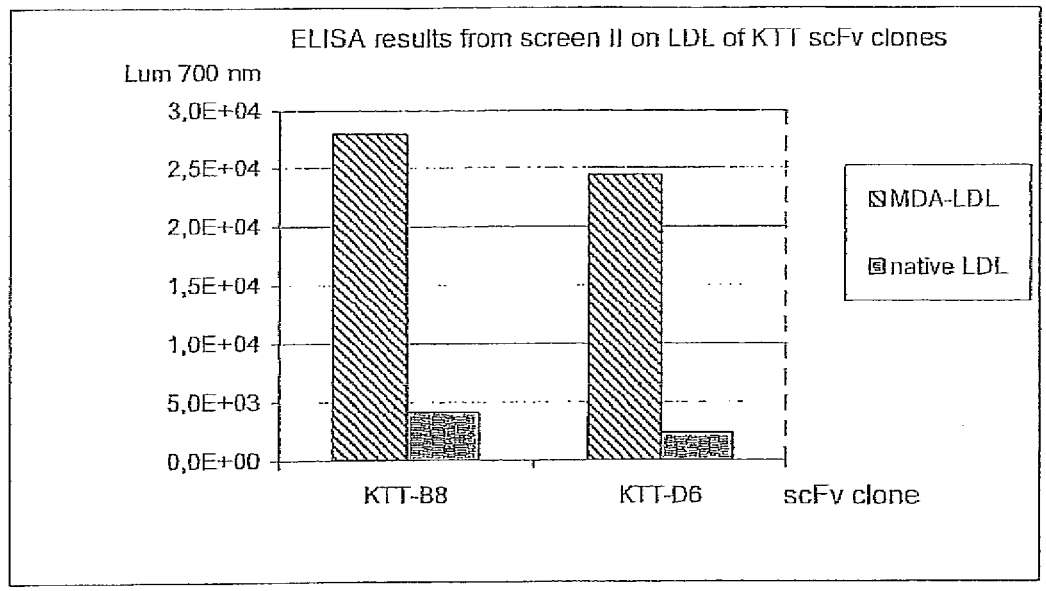
FIG. 1C
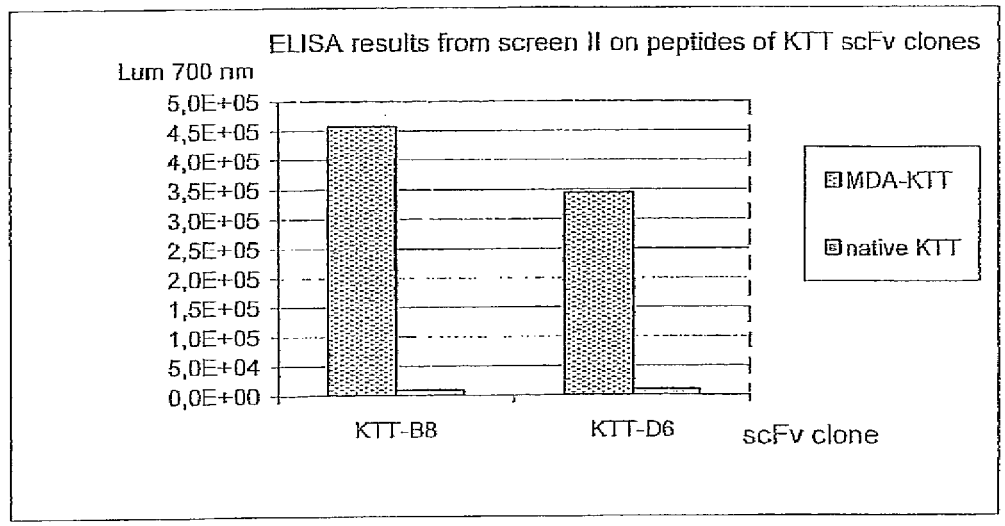
FIG. 1D

FIG. 2
Results from screening III titration of scFv on MDA modified LDL and non-modified native LDL
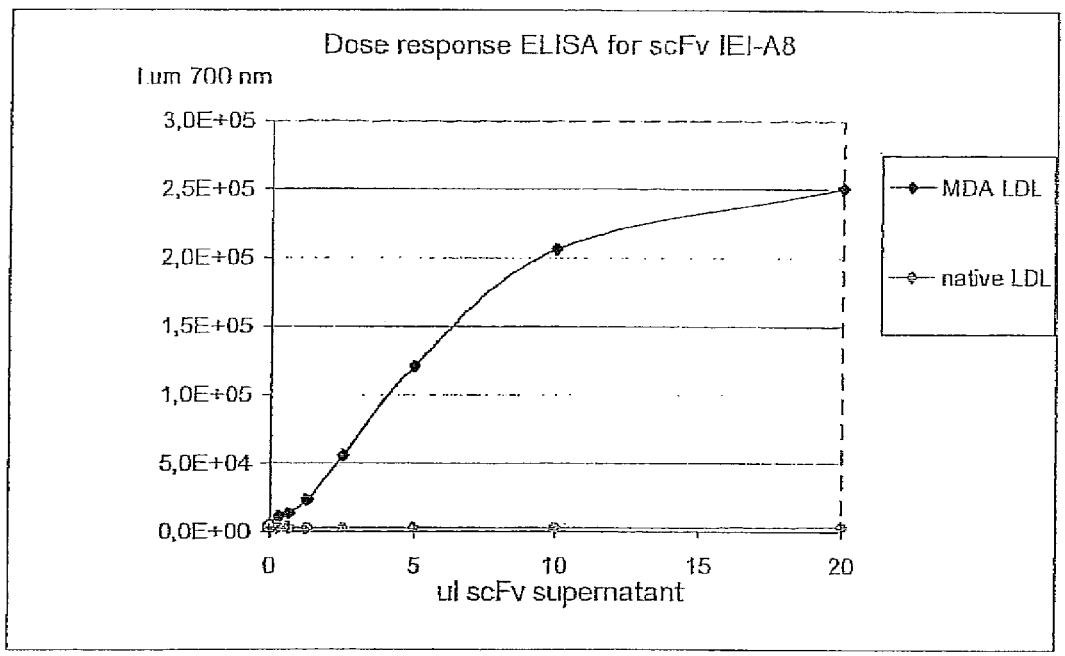
FIG. 2A
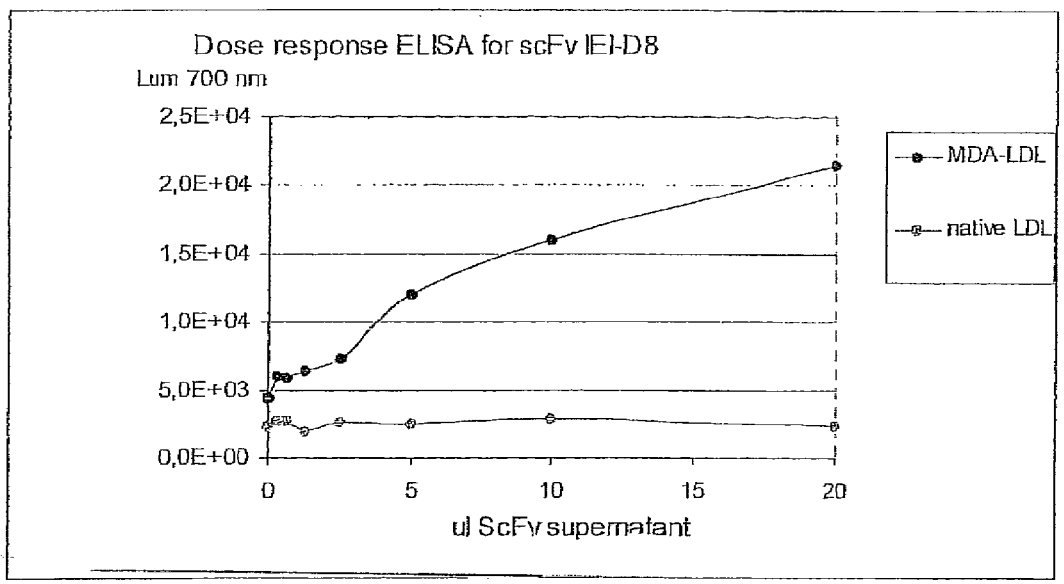
FIG. 2B FIG. 2 cont'd
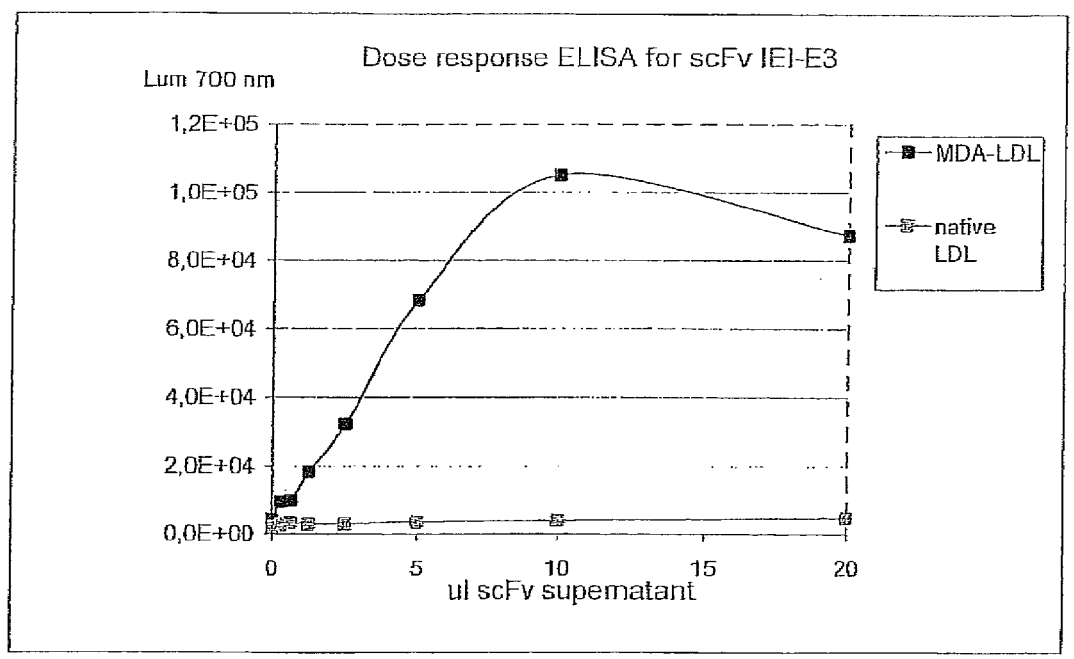
FIG. 2C
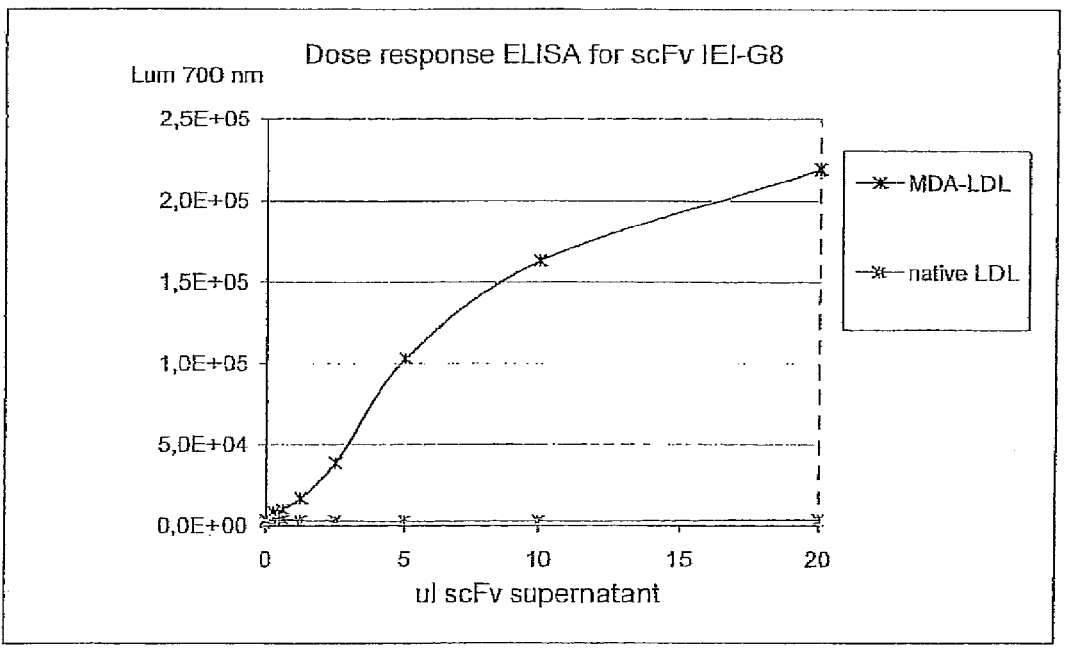
FIG. 2D FIG. 2 cont'd
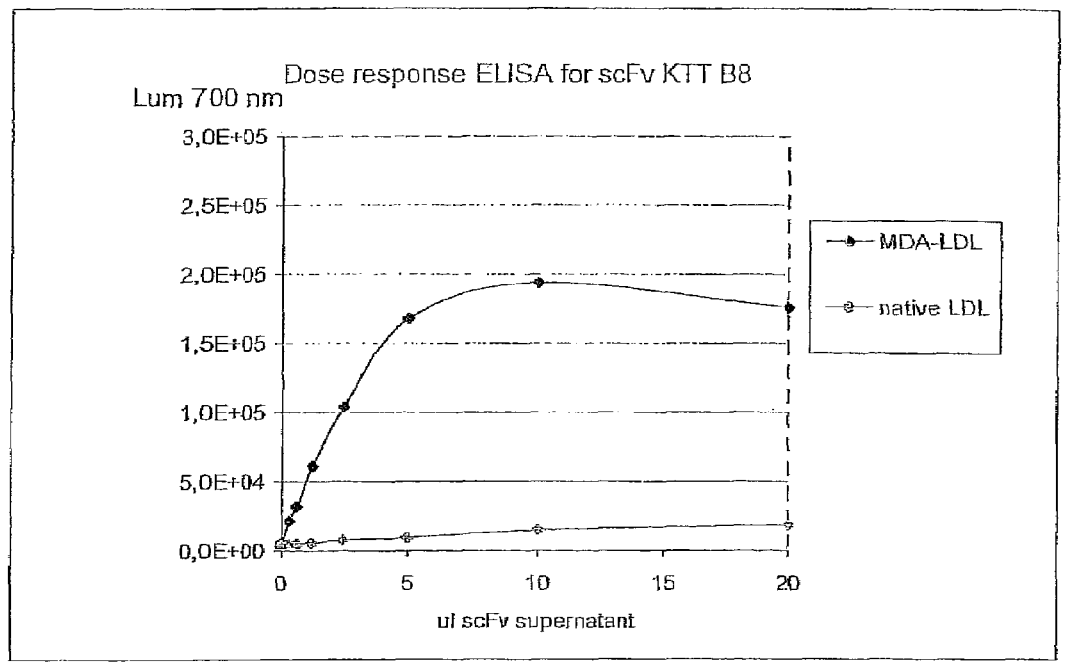
FIG. 2E
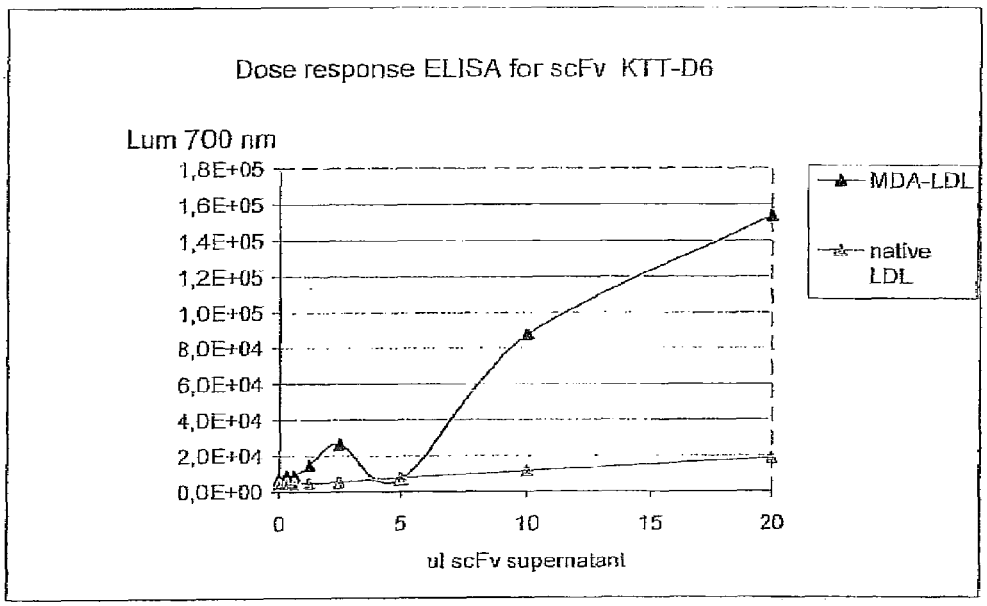
FIG. 2F

FIG. 3

DNA sequences of the variable regions in the six scFv that bind MDA modified ApoB-100 peptides.

IEIA8

Variable heavy region ($V_H$)
GAGGTGCAGCTGTTGGAGTCTGGGGGAGGCTTGGTACAGCCTGGGGGGTCCCTGAGACTCTCC
TGTGCAGCCTCTGGATTCACCTTCAATAACGCCTGGATGAGCTGGGTCCGCCAGGCTCCAGGGA
AGGGGCTGGAGTGGGTCTCATCCATTAGTAGTAGTAGTAGTTACATATACTACGCAGACTCAGT
GAAGGGCCGATTCACCATCTCCAGAGACAATTCCAAGAACACGCTGTATCTGCAAATGAACAGC
CTGAGAGCCGAGGACACTGCCGTGTATTACTGTGCGAGAGTCAGTAGGTACTACTACGGACCAT
CTTTCTACTTTGACTCCTGGGGCCAGGGTACACTGGTCACCGTGAGCAGC

Variable light region ($V_L$)
CAGTCTGTGCTGACTCAGCCACCCTCAGCGTCTGGGACCCCCGGGCAGAGGGTCACCATCTCCT
GCTCTGGAAGCAGGTCCAACATTGGGAATAATTATGTATCCTGGTATCAGCAGCTCCCAGGAAC
GGCCCCCAAACTCCTCATCTATGGTAACAACAATCGGCCCTCAGGGGTCCCTGACCGATTCTCTG
GCTCCAAGTCTGGCACCTCAGCCTCCCTGGCCATCAGTGGGCTCCGGTCCGAGGATGAGGCTG
ATTATTACTGTGCAGCATGGGATGACAGCCTGAATGGTCATTGGGTGTTCGGCGGAGGAACCAA
GCTGACGGTCCTAGGT

IEI-E3

Variable heavy region ($V_H$)
GAGGTGCAGCTGTTGGAGTCTGGGGGAGGCTTGGTACAGCCTGGGGGGTCCCTGAGACTCTCC
TGTGCGGCCTCTGGATTCACCTTCAGTGACTACTACATGAGCTGGGTCCGCCAGGCTCCCGGGA
AGGGGCTGGAGTGGGTATCGGGTGTTAGTTGGAATGGCAGTAGGACGCACTATGCAGACTCTG
TGAAGGGCCGATTCACCATCTCCAGAGACAATTCCAAGAACACGCTGTATCTGCAAATGAACAG
CCTGAGAGCCGAGGACACTGCCGTGTATTACTGTGCGAGAGCGGCTAGGTACTCCTACTACTAC
TACGGTATGGACGTCTGGGGCCAAGGTACACTGGTCACCGTGAGCAGC

Variable light region ($V_L$)
CAGTCTGTGCTGACTCAGCCACCCTCAGCGTCTGGGACCCCCGGGCAGAGGGTCACCATCTCCT
GTTCTGGAAGCAGCTCCAACATCGGAAATAATGCTGTAAACTGGTATCAGCAGCTCCCAGGAAC
GGCCCCCAAACTCCTCATCTATGGGAATGATCGGCGGCCCTCAGGGGTCCCTGACCGATTCTCT
GGCTCCAAGTCTGGCACCTCAGCCTCCCTGGCCATCAGTGGGCTCCGGTCCGAGGATGAGGCT
GATTATTACTGTCAGACCTGGGGCACTGGCCGGGGGTATTCGGCGGAGGAACCAAGCTGACG
GTCCTAGGT FIG. 3 cont'd
IEI-G8

Variable heavy region (V$_H$)
GAGGTGCAGCTGTTGGAGTCTGGGGGAGGCTTGGTACAGCCTGGGGGGTCCCTGAGACTCTCC
TGTGCAGCCTCTGGATTCACCTTTAGTAGCTATTGGATGAGCTGGGTCCGCCAGGCTCCAGGGA
AGGGGCTGGAGTGGGTCTCAAGTATCAGTGGTAGTGGTCGTAGGACATACTACGCAGACTCCGT
GCAGGGCCGGTTCACCATCTCCAGAGACAATTCCAAGAACACGCTGTATCTGCAAATGAACAGC
CTGAGAGCCGAGGACACTGCCGTGTATTACTGTGCGAGATTGGTCTCCTATGGTTCGGGGAGTT
TCGGTTTTGACTACTGGGGCCAAGGTACACTGGTCACCGTGAGCAGC

Variable light region (V$_L$)
CAGTCTGTGCTGACTCAGCCACCCTCAGCGTCTGGGACCCCCGGGCAGAGGGTCACCATCTCTT
GTTCTGGAAGCAGCTCCAATATCGGAAGTAATTATGTATCCTGGTATCAGCAGCTCCCAGGAACG
GCCCCCAAACTCCTCATCTATGGTAACTACAATCGGCCCTCAGGGGTCCCTGACCGATTCTCTGG
CTCCAAGTCTGGCACCTCAGCCTCCCTGGCCATCAGTGGGCTCCGGTCCGAGGATGAGGCTGAT
TATTACTGTGCAGCATGGGATGACAGCCTGAGTGGTTGGGTGTTCGGCGGAGGAACCAAGCTG
ACGGTCCTAGGT

IEI-D8

Variable heavy region (V$_H$)
GAGGTGCAGCTGTTGGAGTCTGGGGGAGGCTTGGTACAGCCTGGGGGGTCCCTGAGACTCTCC
TGTGCAGCCTCTGGATTCACCTTCAGTAACGCCTGGATGAGCTGGGTCCGCCAGGTTCCAGGGA
AGGGGCTGGAGTGGGTCTCAACTCTTGGTGGTAGTGGTGGTGGTAGCACATACTACGCAGACTC
CGTGAAGGGCCGGTTCACCATCTCCAGAGACAATTCCAAGAACACGCTGTATCTGCAAATGAAC
AGCCTGAGAGCCGAGGACACTGCCGTGTATTACTGTGCGAAGTTAGGGGGGCGATCCCGATAT
GGGCGGTGGCCCCGCCAATTTGACTACTGGGGCCAAGGTACACTGGTCACCGTGAGCAGC

Variable light region (V$_L$)
CAGTCTGTGCTGACTCAGCCACCCTCAGCGTCTGGGACCCCCGGGCAGAGGGTCACCATCTCCT
GCTCTGGAAGCAGCTCCAACATTGGAAATAACTATGTATCCTGGTATCAGCAGCTCCCAGGAAC
GGCCCCCAAACTCCTCATCTATAGTAATAATCAGCGGCCCTCAGGGGTCCCTGACCGATTCTCTG
GCTCCAAGTCTGGCACCTCAGCCTCCCTGGCCATCAGTGGGCTCCGGTCCGAGGATGAGGCTG
ATTATTACTGTGCAGCATGGGATGACAGCCTGAGTCATTGGCTGTTCGGCGGAGGAACCAAGCT
GACGGTCCTAGGT

KTT-D6

Variable heavy region (V$_H$)
GAGGTGCAGCTGTTGGAGTCTGGGGGAGGCTTGGTACAGCCTGGGGGGTCCCTGAGACTCTCC
TGTGCAGCCTCTGGATTCACCTTCAGTGACTACTACATGAGCTGGATCCGCCAGGCTCCAGGGA
AGGGGCTGGAGTGGGTCTCAAGTATCAGTGGCCGTGGGGGTAGTTCCTACTACGCAGACTCCG
TGAGGGGCCGGTTCACCATCTCCAGAGACAATTCCAAGAACACGCTGTATCTGCAAATGAACAG
CCTGAGAGCCGAGGACACTGCCGTGTATTACTGTGCGAGACTTTCCTACAGCTATGGTTACGAG
GGGGCCTACTACTTTGACTACTGGGGCCAGGGTACACTGGTCACCGTGAGCAGC

Variable light region (V$_L$)
CAGTCTGTGCTGACTCAGCCACCCTCAGCGTCTGGGACCCCCGGGCAGAGGGTCACCATCTCCT
GCTCTGGAAGCAGCTCCAACATTGGGAATAATTATGTATCCTGGTATCAGCAGCTCCCAGGAAC
GGCCCCCAAACTCCTCATCTATAGGAATAATCAGCGGCCCTCAGGGGTCCCTGACCGATTCTCT
GGCTCCAAGTCTGGCACCTTAGCCTCCCTGGCCATCAGTGGGCTCCGGTCCGAGGATGAGGCT
GATTATTACTGTGCAACCTGGGATGACAGCCTGAATGGTTGGGTGTTCGGCGGAGGAACCAAGC
TGACGGTCCTAGGT FIG. 3 cont'd
KTT-B8

Variable heavy region (V$_H$)
GAGGTGCAGCTGTTGGAGTCTGGGGGAGGCTTGGTACAGCCTGGGGGGTCCCTGAGACTCTCC
TGTGCAGCCTCTGGATTCACCTTTAGCAGCTATGCCATGAGCTGGGTCCGCCAGGCTCCAGGGA
AGGGGCTGGAGTGGGTCTCATCCATTAGTAGTAGTGGTCGTTTCATTTACTACGCAGACTCAATG
AAGGGCCGCTTCACCATCTCCAGAGACAATTCCAAGAACACGCTGTATCTGCAAATGAACAGCCT
GAGAGCCGAGGACACTGCCGTGTATTACTGTACGAGGCTCCGGAGAGGGAGCTACTTCTGGGC
TTTTGATATCTGGGGCCAAGGTACACTGGTCACCGTGAGCAGC

Variable light region (V$_L$)
CAGTCTGTGCTGACTCAGCCACCCTCAGCGTCTGGGACCCCCGGGCAGAGGGTCACCATCTCCT
GTTCTGGAAGCAGCTCCAACATTGGCGGTGAGTCTGTATCCTGGTATCAGCAGCTCCCAGGAAC
GGCCCCCAAACTCCTCATCTATAGTAATAATCAGCGGCCCTCAGGGGTCCCTGACCGATTCTCTG
GCTCCAAGTCTGGCACCTCAGCCTCCCTGGCCATCAGTGGGCTCCGGTCCGAGGATGAGGCTG
ATTATTACTGTGCAGCATGGGATGACAGCCTGAATGGTTGGGTGTTCGGCGGAGGAACCAAGCT
GACGGTCCTAGGT

1-B12

Variable heavy (V$_H$) region

GAGGTGCAGCTGTTGGAGTCTGGGGGAGGCTTGGTACAGCCTGGGGGGTCCCTGAGACTC
TCCTGTGCAGCCTCTGGATTCACCTTTAGAACGTATTGGATGACCTGGGTCCGCCAGGCT
CCAGGGAAGGGGCTGGAGTGGGTCTCATCTATTAGCAGTAGCAGTAATTACATATTCTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGACTCAGA
CGGAGCAGCTGGTACGGGGGGTACTGGTTCGACCCCTGGGGCCAAGGTACACTGGTCACC
GTGAGCTCA

Variable light (V$_L$) region

CAGTCTGTGCTGACTCAGCCACCCTCAGCGTCTGGGACCCCCGGGCAGAGGGTCACCATC
TCCTGCTCTGGAAGCAGCTCCAACATTGGGAATAATTATGTATCCTGGTATCAGCAGCTC
CCAGGAACGGCCCCCAAACTCCTCATCTATAGGAATAATCAGCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGCCTGAATGGTCATTGG
GTGTTCGGCGGAGGAACCAAGCTGACGGTCCTAGGT

FIG. 3 cont'd
Clone: 1-C07

Variable heavy (V$_H$) region

GAGGTGCAGCTGTTGGAGTCTGGGGGAGGCTTGGTACAGCCTGGGGGGTCCCTGAGACTCT
CCTGTGCAGCCTCTGGATTCACCTTCAGTAGCAACTACATGAGCTGGGTCCGCCAGGCTCC
AGGGAAGGGGCTGGAGTGGGTCTCATCCATTAGTAGTAGTAGTAGTTACATATACTACGCA
GACTCAGTGAAGGGCCGATTCACCATCTCCAGAGACAATTCCAAGAACACGCTGTATCTGC
AAATGAACAGCCTGAGAGCCGAGGACACTGCCGTGTATTACTGTGCGAGAGTAGGCCGGTA
TAACTGGAAGACGGGGCATGCTTTTGATATCTGGGGCCAGGGTACACTGGTCACCGTGAGC
TCA

Variable light region (V$_L$)

CAGTCTGTGCTGACTCAGCCACCCTCAGCGTCTGGGACCCCCGGGCAGAGGGTCACCATCT
CCTGCTCTGGAAGGACCTACAACATTGGAAATAATTATGTATCGTGGTATCAGCAGCTCCC
AGGAACGGCCCCCAAACTCCTCATCTATGGTAACATCAATCGGCCCTCAGGGGTCCCTGAC
CGATTCTCTGGCTCCAAGTCTGGCACCTCAGCCTCCCTGGCCATCAGTGGGCTCCGGTCCG
AGGATGAGGCTGATTATTACTGTGCAGCATGGGATGTCAGGCTGAATGGTTGGGTGTTCGG
CGGAGGAACCAAGCTGACGGTCCTAGGT

Clone: 1-C12

Variable heavy (V$_H$) region

GAGGTGCAGCTGTTGGAGTCTGGGGGAGGCTTGGTACAGCCTGGGGGGTCCCTGAGACTC
TCCTGTGCAGCCTCTGGATTCACCTTCCGTGACTACTACGTGAGCTGGATCCGCCAGGCT
CCAGGGAAGGGGCTGGAGTGGGTCTCAAGTATTAGTGGTAGTGGGGGTAGGACATACTAC
GCAGACTCCGTGGAGGGCCGGTTCACCATCTCCAGAGACAATTCCAAGAACACGCTGTAT
CTGCAAATGAACAGCCTGAGAGCCGAGGACACTGCCATGTATTACTGTGCCAGAGTATCC
GCCCTTCGGAGACCCATGACTACAGTAACTACTTACTGGTTCGACCCCTGGGGCCAAGGT
ACACTGGTCACCGTGAGCTCA

Variable light region (V$_L$)

CAGTCTGTGCTGACTCAGCCACCCTCAGCGTCTGGGACCCCCGGGCAGAGGGTCACCATC
TCCTGCTCTGGAAGGAGCTCCAACATTGGGAATAGTTATGTCTCCTGGTATCAGCAGCTC
CCAGGAACGGCCCCCAAACTCCTCATCTATAGGAATAATCAGCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGGATGGGATGACACCCTGCGTGCTTGGGTG
TTCGGCGGAGGAACCAAGCTGACGGTCCTAGGT

FIG. 3 cont'd
Clone: 1-G10

Variable heavy (V$_H$) region

GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCCGCTATTAGTGGTAGTGGTAACACATACTATGCA
GACTCCGTGAAGGGCCGGTTCACCATCTCCAGAGACAATTCCAAGAACACGCTGTATCTG
CAAATGAACAGCCTGAGAGCCGAGGACACTGCCGTGTATTACTGTGCGAGAGCCTCCCAC
CGTATATTAGGTTATGCTTTTGATATCTGGGGCCAGGGTACACTGGTCACCGTGAGCTCA

Variable light region (V$_L$)

CAGTCTGTGCTGACTCAGCCACCCTCAGCGTCTGGGACCCCCGGGCAGAGGGTCACCATC
TCTTGTTCTGGAAGCCGCTCCAACATCGGGAGAAATGCTGTTAGTTGGTATCAGCAGCTC
CCAGGAACGGCCCCCAAACTCCTCATCTATGCTAACAGCAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGGCAGCCTGAATGGTTGGGTG
TTCGGCGGAGGAACCAAGCTGACGGTCC

Clone: 2-D03

Variable heavy (V$_H$) region

GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCAAGTATTAGTGTTGGTGGACATAGGACATATTAT
GCAGATTCCGTGAAGGGCCGGTCCACCATCTCCAGAGACAATTCCAAGAACACGCTGTAT
CTGCAAATGAACAGCCTGAGAGCCGAGGACACTGCCGTGTATTACTGTGCACGGATACGG
GTGGGTCCGTCCGGCGGGGCCTTTGACTACTGGGGCCAGGGTACACTGGTCACCGTGAGC
TCA

Variable light region (V$_L$)

CAGTCTGTGCTGACTCAGCCACCCTCAGCGTCTGGGACCCCCGGGCAGAGGGTCACCAT
CTCCTGCTCTGGAAGCAACACCAACATTGGGAAGAACTATGTATCTTGGTATCAGCAGC
TCCCAGGAACGGCCCCCAAACTCCTCATCTATGCTAATAGCAATCGGCCCTCAGGGGTC
CCTGACCGATTCTCTGGCTCCAAGTCTGGCACCTCAGCCTCCCTGGCCATCAGTGGGCT
CCGGTCCGAGGATGAGGCTGATTATTACTGTGCGTCATGGGATGCCAGCCTGAATGGTT
GGGTATTCGGCGGAGGAACCAAGCTGACGGTCCTAGGT

FIG. 3 cont'd
Clone: 2-F07

Variable heavy (V_H) region

GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATCCACCATCTCCAGAGACAATTCCAAGAACACGCTGTAT
CTGCAAATGAACAGCCTGAGAGCCGAGGACACTGCCGTGTATTACTGTGCGAGGCTCACA
AATATTTTGACTGGTTATTATACCTCAGGATATGCTTTTGATATCTGGGGCCAAGGTACA
CTGGTCACCGTGAGCTCA

Variable light region (V_L)

CAGTCTGTGCTGACTCAGCCACCCTCAGCGTCTGGGACCCCCGGGCAGAGGGTCACCATC
TCCTGCTCTGGAAGCACCTCCAACATTGGGAAGAATTATGTATCCTGGTATCAGCAGCTC
CCAGGAACGGCCCCCAAACTCCTCATCTATGGTAACAGCAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGCCAGCCTCAGTGGTTGGGTG
TTCGGCGGAGGAACCAAGCTGACGGTCCTAGGT

Clone: 2-F09

Variable heavy (V_H) region

GAGGTGCAGCTGTTGGAGTCTGGGGGAGGCTTGGTACAGCCTGGGGGGTCCCTGAGACTC
TCCTGTGCAGCCTCTGGATTCACCTTCAGTAGTTCTTGGATGAGTTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGAGTAGGG
AACTACGGTTTCTACCACTACATGGACGTCTGGGGCCAAGGTACACTGGTCACCGTGAGC
TCA

Variable light region (V_L)

CAGTCTGTGCTGACTCAGCCACCCTCAGCGTCTGGGACCCCCGGGCAGAGGGTCACCATC
TCTTGTTCTGGAGGCAGCTCAAACATCGGAAAAGAGGTGTAAATTGGTATCAGCAGCTC
CCAGGAACGGCCCCCAAACTCCTCATCTATGGTAACAGAAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCTACATGGGATTACAGCCTCAATGCTTGGGTG
TTCGGCGGAGGAACCAAGCTGACGGTCCTAGGT

FIG. 3 cont'd
Clone: 4-A02

Variable heavy (V$_H$) region

GAGGTGCAGCTGTTGGAGTCTGGGGGAGGCTTGGTACAGCCTGGGGGGTCCCTGAGACTC
TCCTGTGCAGCCTCTGGATTCACCTTTAGTAGCTATTGGATGAGCTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGAATTAAA
CGGTTACGATTCGGCTGGACCCCTTTTGACTACTGGGGCCAGGGTACACTGGTCACCGTG
AGCTCA

Variable light region (V$_L$)

CAGTCTGTTCTGACTCAGCCACCCTCAGCGTCTGGGACCCCCGGGCAGAGGGTCACCATC
TCCTGTTCTGGAAGCAGCTCCAACATCGGAAATAATGGTGTAAACTGGTATCAGCAGCTC
CCAGGAACGGCCCCCAAACTCCTCATCTATGGTAACAACAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGCCTGCGTGGTTGGCTG
TTCGGCGGAGGAACCAAGCTGACGGTCCTAGGT

Clone. 4-C03
Variable heavy (V$_H$) region

GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGAGTCAAT
AGCAAAAAGTGGTATGAGGGCTACTTCTTTGACTACTGGGGCCAGGGTACACTGGTCACC
GTGAGCTCA

Variable light region (V$_L$)

CAGTCTGTGCTGACTCAGCCACCCTCAGCGTCTGGGACCCCCGGGCAGAGGGTCACCATC
TCCTGCTCTGGAAGCAGCTCCAACATTGGGAATAATTATGTATCCTGGTATCAGCAGCTC
CCAGGAACGGCCCCCAAACTCCTCATCTATGGTAACAGCAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGTCTGAGTGGTTGGGTG
TTCGGCGGAGGAACCAAGCTGACGGTCCTAGGT

FIG. 3 cont'd
Clone: 4-D04
Variable heavy (V$_H$) region

GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCATCCATTAGTACTAGTAGTAATTACATATACTAC
GCAGACTCAGTGAAGGGCCGGTTCACCATCTCCAGAGACAATTCCAAGAACACGCTGTAT
CTGCAAATGAACAGCCTGAGAGCCGAGGACACTGCCGTGTATTACTGTGCGAGAGTCAAG
AAGTATAGCAGTGGCTGGTACTCGAATTATGCTTTTGATATCTGGGGCCAAGGTACACTG
GTCACCGTGAGCTCA

Variable light region (V$_L$)

CAGTCTGTGCTGACTCAGCCACCCTCAGCGTCTGGGACCCCCGGGCAGAGGGTCACCATC
TCCTGCTCTGGAAGCAGCTCCAGCATTGGGAATAATTTTGTATCCTGGTATCAGCAGCTC
CCAGGAACGGCCCCCAAACTCCTCATCTATGACAATAATAAGCGACCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGCCTGAATGGTTGGGTG
TTCGGCGGAGGAACCAAGCTGACGGTCCTAGGT

Light Chain Vector

Heavy Chain vector

This graph shows the result from 25 ng purified IgG detected with rabbit-anti-Human IgG-HRP (DAKO P214) and luminescence at 700nm. The plate was coated with 0.5 µg LDL/well.

SEQUENCE LISTING

<160> NUMBER OF SEQ ID NOS: 79

<210> SEQ ID NO 1
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 1

```
gaggtgcagc tgttggagtc tgggggaggc ttggtacagc ctgggggtc cctgagactc      60 tcctgtgcag cctctggatt caccttcaat aacgcctgga tgagctgggt ccgccaggct    120
ccagggaagg ggctggagtg ggtctcatcc attagtagta gtagtagtta catatactac    180
gcagactcag tgaagggccg attcaccatc tccagagaca attccaagaa cacgctgtat    240
ctgcaaatga acagcctgag agccgaggac actgccgtgt attactgtgc gagagtcagt    300
aggtactact acggaccatc tttctacttt gactcctggg gccagggtac actggtcacc    360
gtgagcagc                                                            369
```

<210> SEQ ID NO 2
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 2

```
cagtctgtgc tgactcagcc accctcagcg tctgggaccc ccgggcagag ggtcaccatc     60
tcctgctctg gaagcaggtc caacattggg aataattatg tatcctggta tcagcagctc    120
ccaggaacgg cccccaaact cctcatctat ggtaacaaca atcggccctc aggggtccct    180
gaccgattct ctggctccaa gtctggcacc tcagcctccc tggccatcag tgggctccgg    240
tccgaggatg aggctgatta ttactgtgca gcatgggatg acagcctgaa tggtcattgg    300
gtgttcggcg gaggaaccaa gctgacggtc ctaggt                              336
```

<210> SEQ ID NO 3
<211> LENGTH: 366
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3

```
gaggtgcagc tgttggagtc tgggggaggc ttggtacagc ctgggggtc cctgagactc      60 tcctgtgcgg cctctggatt caccttcagt gactactaca tgagctgggt ccgccaggct    120
cccgggaagg ggctggagtg ggtatcgggt gttagttgga atggcagtag gacgcactat    180
gcagactctg tgaagggccg attcaccatc tccagagaca attccaagaa cacgctgtat    240
ctgcaaatga acagcctgag agccgaggac actgccgtgt attactgtgc gagagcggct    300
aggtactcct actactacta cggtatggac gtctggggc aaggtacact ggtcaccgtg    360
agcagc                                                               366
```

<210> SEQ ID NO 4

<211> LENGTH: 327
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 4
cagtctgtgc tgactcagcc accctcagcg tctgggaccc ccgggcagag ggtcaccatc    60
tcctgttctg gaagcagctc caacatcgga ataatgctg taaactggta tcagcagctc   120
ccaggaacgg cccccaaact cctcatctat gggaatgatc ggcggccctc agggtccct   180 gaccgattct ctggctccaa gtctggcacc tcagcctccc tggccatcag tgggctccgg   240
tccgaggatg aggctgatta ttactgtcag acctggggca ctggccgggg gtattcggc   300 ggaggaacca agctgacggt cctaggt                                      327

<210> SEQ ID NO 5
<211> LENGTH: 366
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 5
gaggtgcagc tgttggagtc tgggggaggc ttggtacagc ctggggggtc cctgagactc    60
tcctgtgcag cctctggatt caccttagt agctattgga tgagctgggt ccgccaggct   120
ccagggaagg ggctggagtg gtctcaagt atcagtggta gtggtcgtag acatactac   180 gcagactccg tgcagggccg gttcaccatc tccagagaca attccaagaa cacgctgtat   240
ctgcaaatga acagcctgag agccgaggac actgccgtgt attactgtgc gagattggtc   300
tcctatggtt cggggagttt cggttttgac tactggggcc aaggtacact ggtcaccgtg   360
agcagc                                                              366

<210> SEQ ID NO 6
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 6
cagtctgtgc tgactcagcc accctcagcg tctgggaccc ccgggcagag ggtcaccatc    60
tcttgttctg gaagcagctc caatatcgga agtaattatg tatcctggta tcagcagctc   120
ccaggaacgg cccccaaact cctcatctat ggtaactaca atcggccctc agggtccct   180 gaccgattct ctggctccaa gtctggcacc tcagcctccc tggccatcag tgggctccgg   240
tccgaggatg aggctgatta ttactgtgca gcatgggatg acagcctgag tggttgggtg   300
ttcggcggag gaaccaagct gacggtccta ggt                                333

<210> SEQ ID NO 7
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 7

```
gaggtgcagc tgttggagtc tgggggaggc ttggtacagc ctgggggtc cctgagactc      60 tcctgtgcag cctctggatt caccttcagt aacgcctgga tgagctgggt ccgccaggtt    120
ccagggaagg ggctggagtg ggtctcaact cttggtggta gtggtggtgg tagcacatac    180
tacgcagact ccgtgaaggg ccggttcacc atctccagag acaattccaa gaacacgctg    240
tatctgcaaa tgaacagcct gagagccgag gacactgccg tgtattactg tgcgaagtta    300 gggggggcgat cccgatatgg gcggtggccc cgccaatttg actactgggg ccaaggtaca    360
ctggtcaccg tgagcagc                                                  378

<210> SEQ ID NO 8
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 8
cagtctgtgc tgactcagcc accctcagcg tctgggaccc ccgggcagag ggtcaccatc      60
tcctgctctg gaagcagctc caacattgga aataactatg tatcctggta tcagcagctc    120
ccaggaacgg ccccccaaact cctcatctat agtaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tcattggctg    300
ttcggcggag gaaccaagct gacggtccta ggt                                 333

<210> SEQ ID NO 9
<211> LENGTH: 372
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 9
gaggtgcagc tgttggagtc tgggggaggc ttggtacagc ctgggggtc cctgagactc      60 tcctgtgcag cctctggatt caccttcagt gactactaca tgagctggat ccgccaggct    120
ccagggaagg ggctggagtg ggtctcaagt atcagtggcc gtgggggtag ttcctactac    180
gcagactccg tgaggggccg gttcaccatc tccagagaca attccaagaa cacgctgtat    240
ctgcaaatga acagcctgag agccgaggac actgccgtgt attactgtgc gagactttcc    300
tacagctatg gttacgaggg ggcctactac tttgactact ggggccaggg tacactggtc    360
accgtgagca gc                                                        372

<210> SEQ ID NO 10
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 10
cagtctgtgc tgactcagcc accctcagcg tctgggaccc ccgggcagag ggtcaccatc      60
tcctgctctg gaagcagctc caacattggg aataattatg tatcctggta tcagcagctc    120
ccaggaacgg ccccccaaact cctcatctat aggaataatc agcggccctc aggggtccct    180
```

-continued

```
gaccgattct ctggctccaa gtctggcacc ttagcctccc tggccatcag tgggctccgg    240
tccgaggatg aggctgatta ttactgtgca acctgggatg acagcctgaa tggttgggtg    300
ttcggcggag gaaccaagct gacggtccta ggt                                 333
```

<210> SEQ ID NO 11
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 11

```
gaggtgcagc tgttggagtc tgggggaggc ttggtacagc ctggggggtc cctgagactc    60
tcctgtgcag cctctggatt cacctttagc agctatgcca tgagctgggt ccgccaggct    120
ccagggaagg gctggagtg gtctcatcc attagtagta gtggtcgttt catttactac    180
gcagactcaa tgaagggccg cttcaccatc tccagagaca attccaagaa cacgctgtat    240
ctgcaaatga acagcctgag agccgaggac actgccgtgt attactgtac gaggctccgg    300
agagggagct acttctgggc ttttgatatc tggggccaag gtacactggt caccgtgagc    360
agc                                                                  363
```

<210> SEQ ID NO 12
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 12

```
cagtctgtgc tgactcagcc accctcagcg tctgggaccc ccgggcagag ggtcaccatc    60
tcctgttctg gaagcagctc caacattggc ggtgagtctg tatcctggta tcagcagctc    120
ccaggaacgg cccccaaact cctcatctat agtaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgaa tggttgggtg    300
ttcggcggag gaaccaagct gacggtccta ggt                                 333
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
ggtgtgcatt ccgaggtgca gctgttggag                                     30
```

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gacgtacgac tcacctgagc tcacggtgac cag                                33
```

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
ggtgtgcatt cccagtctgt gctgactcag                                    30
```

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
gacgtacgtt ctactcacct aggaccgtca gctt                               34
```

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
atgggtgaca atgacatc                                                 18
```

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
aagcttgcta gcgtacg                                                  17
```

<210> SEQ ID NO 19
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 19

```
gaggtgcagc tgttggagtc tgggggaggc ttggtacagc ctggggggtc cctgagactc   60
tcctgtgcag cctctggatt caccttaga acgtattgga tgacctgggt ccgccaggct  120
ccagggaagg ggctggagtg ggtctcatct attagcagta gcagtaatta catattctac  180
gcagactcag tgaagggccg attcaccatc tccagagaca attccaagaa cacgctgtat  240
ctgcaaatga acagcctgag agccgaggac actgccgtgt attactgtgc gagactcaga  300
cggagcagct ggtacggggg gtactggttc gaccccctggg gccaaggtac actggtcacc  360
gtgagctca                                                          369
```

<210> SEQ ID NO 20
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 20

```
cagtctgtgc tgactcagcc accctcagcg tctgggaccc ccgggcagag ggtcaccatc    60
tcctgctctg gaagcagctc caacattggg aataattatg tatcctggta tcagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgaa tggtcattgg   300
gtgttcggcg gaggaaccaa gctgacggtc ctaggt                             336
```

<210> SEQ ID NO 21
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 21

```
gaggtgcagc tgttggagtc tgggggaggc ttggtacagc ctgggggtc cctgagactc      60 tcctgtgcag cctctggatt caccttcagt agcaactaca tgagctgggt ccgccaggct   120
ccagggaagg gctggagtg gtctcatcc attagtagta gtagtagtta catatactac     180
gcagactcag tgaagggccg attcaccatc tccagagaca attccaagaa cacgctgtat   240
ctgcaaatga acagcctgag agccgaggac actgccgtgt attactgtgc gagagtaggc   300
cggtataact ggaagacggg gcatgctttt gatatctggg gccagggtac actggtcacc   360
gtgagctca                                                           369
```

<210> SEQ ID NO 22
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 22

```
cagtctgtgc tgactcagcc accctcagcg tctgggaccc ccgggcagag ggtcaccatc    60
tcctgctctg gaaggaccta caacattgga aataattatg tatcgtggta tcagcagctc   120
ccaggaacgg cccccaaact cctcatctat ggtaacatca atcggccctc aggggtccct   180
gaccgattct ctggctccaa gtctggcacc tcagcctccc tggccatcag tgggctccgg   240
tccgaggatg aggctgatta ttactgtgca gcatgggatg tcaggctgaa tggttgggtg   300
ttcggcggag gaaccaagct gacggtccta ggt                                333
```

<210> SEQ ID NO 23
<211> LENGTH: 381
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 23

```
gaggtgcagc tgttggagtc tgggggaggc ttggtacagc ctgggggtc cctgagactc      60
tcctgtgcag cctctggatt caccttccgt gactactacg tgagctggat ccgccaggct    120
ccagggaagg ggctggagtg ggtctcaagt attagtggta gtgggggtag acatactac    180
gcagactccg tggagggccg gttcaccatc tccagadaca attccaagaa cacgctgtat    240
ctgcaaatga acagcctgag agccgaggac actgccatgt attactgtgc cagagtatcc    300
gcccttcgga gacccatgac tacagtaact acttactggt tcgacccctg gggccaaggt    360
acactggtca ccgtgagctc a                                              381
```

<210> SEQ ID NO 24
<211> LENGTH: 333
<212> TYPE: DNA
<213> ORGANISM: Artificial Sequence
<220> FEATURE:
<223> OTHER INFORMATION: Description of Artificial Sequence: Synthetic
   nucleotide sequence

<400> SEQUENCE: 24

```
cagtctgtgc tgactcagcc accctcagcg tctgggaccc ccgggcagag ggtcaccatc      60
tcctgctctg gaaggagctc caacattggg aatagttatg tctcctggta tcagcagctc    120
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca ggatgggatg acaccctgcg tgcttgggtg    300
ttcggcggag gaaccaagct gacggtccta ggt                                  333
```

<210> SEQ ID NO 25
<211> LENGTH: 360
<212> TYPE: DNA
<213> ORGANISM: Artificial Sequence
<220> FEATURE:
<223> OTHER INFORMATION: Description of Artificial Sequence: Synthetic
   nucleotide sequence

<400> SEQUENCE: 25

```
gaggtgcagc tgttggagtc tgggggaggc ttggtacagc ctgggggtc cctgagactc      60
tcctgtgcag cctctggatt caccttcagt aacgcctgga tgagctgggt ccgccaggct    120
ccagggaagg ggctggagtg ggtctccgct attagtggta gtggtaacac atactatgca    180
gactccgtga agggccggtt caccatctcc agagacaatt ccaagaacac gctgtatctg    240
caaatgaaca gcctgagagc cgaggacact gccgtgtatt actgtgcgag agcctcccac    300
cgtatattag gttatgcttt tgatatctgg ggccagggta cactggtcac cgtgagctca    360
```

<210> SEQ ID NO 26
<211> LENGTH: 328
<212> TYPE: DNA
<213> ORGANISM: Artificial Sequence
<220> FEATURE:
<223> OTHER INFORMATION: Description of Artificial Sequence: Synthetic
   nucleotide sequence

<400> SEQUENCE: 26

```
cagtctgtgc tgactcagcc accctcagcg tctgggaccc ccgggcagag ggtcaccatc      60
tcttgttctg gaagccgctc caacatcggg agaaatgctg ttagttggta tcagcagctc    120
ccaggaacgg cccccaaact cctcatctat gctaacagca atcggccctc aggggtccct    180
```

```
gaccgattct ctggctccaa gtctggcacc tcagcctccc tggccatcag tgggctccgg      240
tccgaggatg aggctgatta ttactgtgca gcatgggatg gcagcctgaa tggttgggtg      300
ttcggcggag gaaccaagct gacggtcc                                        328

<210> SEQ ID NO 27
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 27
gaggtgcagc tgttggagtc tgggggaggc ttggtacagc ctgggggggtc cctgagactc      60 tcctgtgcag cctctggatt caccttcagt aacgcctgga tgagctgggt ccgccaggct     120
ccagggaagg gctggagtg gtctcaagt attagtgttg gtggacatag gacatattat       180
gcagattccg tgaagggccg gtccaccatc tccagagaca attccaagaa cacgctgtat     240
ctgcaaatga acagcctgag agccgaggac actgccgtgt attactgtgc acggatacgg     300
gtgggtccgt ccggcggggc ctttgactac tggggccagg gtacactggt caccgtgagc     360
tca                                                                  363

<210> SEQ ID NO 28
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 28
cagtctgtgc tgactcagcc accctcagcg tctgggaccc ccgggcagag ggtcaccatc      60
tcctgctctg gaagcaacac caacattggg aagaactatg tatcttggta tcagcagctc     120
ccaggaacgg cccccaaact cctcatctat gctaatagca atcggccctc aggggtccct     180
gaccgattct ctggctccaa gtctggcacc tcagcctccc tggccatcag tgggctccgg     240
tccgaggatg aggctgatta ttactgtgcg tcatgggatg ccagcctgaa tggttgggta     300
ttcggcggag gaaccaagct gacggtccta ggt                                  333

<210> SEQ ID NO 29
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 29
gaggtgcagc tgttggagtc tgggggaggc ttggtacagc ctgggggggtc cctgagactc      60 tcctgtgcag cctctggatt caccttcagt aacgcctgga tgagctgggt ccgccaggct     120
ccagggaagg gctggagtg gtctcatcc attagtagta gtagtagtta catatactac      180
gcagactcag tgaagggccg atccaccatc tccagagaca attccaagaa cacgctgtat     240
ctgcaaatga acagcctgag agccgaggac actgccgtgt attactgtgc gaggctcaca     300
aatattttga ctggttatta tacctcagga tatgcttttg atatctgggg ccaaggtaca     360
ctggtcaccg tgagctca                                                  378
```

<210> SEQ ID NO 30
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 30
cagtctgtgc tgactcagcc accctcagcg tctgggaccc ccgggcagag ggtcaccatc      60
tcctgctctg gaagcacctc caacattggg aagaattatg tatcctggta tcagcagctc     120
ccaggaacgg cccccaaact cctcatctat ggtaacagca atcggccctc agggqtccct     180 gaccgattct ctggctccaa gtctggcacc tcagcctccc tggccatcag tgggctccgg     240
tccgaggatg aggctgatta ttactgtgca gcatgggatg ccagcctcag tggttgggtg     300
ttcggcggag gaaccaagct gacggtccta ggt                                  333

<210> SEQ ID NO 31
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 31
gaggtgcagc tgttggagtc tgggggaggc ttggtacagc ctgggggqtc cctgagactc      60 tcctgtgcag cctctggatt caccttcagt agttcttgga tgagttgggt ccgccaggct     120
ccagggaagg ggctggagtg gtctcatcc attagtagta gtagtagtta catatactac     180
gcagactcag tgaagggccg attcaccatc tccagagaca attccaagaa cacgctgtat     240
ctgcaaatga acagcctgag agccgaggac actgccgtgt attactgtgc gagagtaggg     300
aactacggtt tctaccacta catggacgtc tggggccaag gtacactggt caccgtgagc     360
tca                                                                  363

<210> SEQ ID NO 32
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 32
cagtctgtgc tgactcagcc accctcagcg tctgggaccc ccgggcagag ggtcaccatc      60
tcttgttctg gaggcagctc aaacatcgga aaaagaggtg taaattggta tcagcagctc     120
ccaggaacgg cccccaaact cctcatctat ggtaacagaa atcggccctc agggqtccct     180 gaccgattct ctggctccaa gtctggcacc tcagcctccc tggccatcag tgggctccgg     240
tccgaggatg aggctgatta ttactgtgct acatgggatt acagcctcaa tgcttgggtg     300
ttcggcggag gaaccaagct gacggtccta ggt                                  333

<210> SEQ ID NO 33
<211> LENGTH: 366
<212> TYPE: DNA
<213> ORGANISM: Artificial Sequence
<220> FEATURE:
<223> OTHER INFORMATION: Description of Artificial Sequence: Synthetic -continued nucleotide sequence

<400> SEQUENCE: 33

```
gaggtgcagc tgttggagtc tgggggaggc ttggtacagc ctggggggtc cctgagactc      60
tcctgtgcag cctctggatt cacctttagt agctattgga tgagctgggt ccgccaggct     120
ccagggaagg ggctggagtg ggtctcatcc attagtagta gtagtagtta catatactac     180
gcagactcag tgaagggccg attcaccatc tccagagaca attccaagaa cacgctgtat     240
ctgcaaatga acagcctgag agccgaggac actgccgtgt attactgtgc gagaattaaa     300
cggttacgat tcggctggac ccctttgac tactggggcc aggtacact ggtcaccgtg       360
agctca                                                               366
```

<210> SEQ ID NO 34
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 34

```
cagtctgttc tgactcagcc accctcagcg tctgggaccc ccgggcagag ggtcaccatc      60
tcctgttctg gaagcagctc caacatcgga ataatggtg taaactggta tcagcagctc     120
ccaggaacgg cccccaaact cctcatctat ggtaacaaca atcggccctc aggggtccct     180
gaccgattct ctggctccaa gtctggcacc tcagcctccc tggccatcag tgggctccgg     240
tccgaggatg aggctgatta ttactgtgca gcatgggatg acagcctgcg tggttggctg     300
ttcggcggag gaaccaagct gacggtccta ggt                                  333
```

<210> SEQ ID NO 35
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 35

```
gaggtgcagc tgttggagtc tgggggaggc ttggtacagc ctggggggtc cctgagactc      60
tcctgtgcag cctctggatt cacccttcagt aacgcctgga tgagctgggt ccgccaggct   120
ccagggaagg ggctggagtg ggtctcatcc attagtagta gtagtagtta catatactac    180
gcagactcag tgaagggccg attcaccatc tccagagaca attccaagaa cacgctgtat    240
ctgcaaatga acagcctgag agccgaggac actgccgtgt attactgtgc gagagtcaat    300
agcaaaaagt ggtatgaggg ctacttcttt gactactggg gccagggtac actggtcacc    360
gtgagctca                                                            369
```

<210> SEQ ID NO 36
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 36

```
cagtctgtgc tgactcagcc accctcagcg tctgggaccc ccgggcagag ggtcaccatc      60
```

-continued

```
tcctgctctg aagcagctc caacattggg aataattatg tatcctggta tcagcagctc      120
ccaggaacgg cccccaaact cctcatctat ggtaacagca atcggccctc agggqtccct     180 gaccgattct ctggctccaa gtctggcacc tcagcctccc tggccatcag tgggctccgg     240
tccgaggatg aggctgatta ttactgtgca gcatgggatg acagtctgag tggttgggtg     300
ttcggcggag gaaccaagct gacggtccta ggt                                  333
```

<210> SEQ ID NO 37
<211> LENGTH: 375
<212> TYPE: DNA
<213> ORGANISM: Artificial Sequence
<220> FEATURE:
<223> OTHER INFORMATION: Description of Artificial Sequence: Synthetic
     nucleotide sequence

<400> SEQUENCE: 37

```
gaggtgcagc tgttggagtc tgggggaggc ttggtacagc ctgggggtc cctgagactc       60 tcctgtgcag cctctggatt caccttcagt aacgcctgga tgagctgggt ccgccaggct     120
ccagggaagg ggctggagtg gtctcatcc attagtacta gtagtaatta catatactac      180
gcagactcag tgaagggccg gttcaccatc tccagagaca attccaagaa cacgctgtat    240
ctgcaaatga acagcctgag agccgaggac actgccgtgt attactgtgc gagagtcaag    300
aagtatagca gtggctggta ctcgaattat gcttttgata tctggggcca aggtacactg    360
gtcaccgtga gctca                                                      375
```

<210> SEQ ID NO 38
<211> LENGTH: 333
<212> TYPE: DNA
<213> ORGANISM: Artificial Sequence
<220> FEATURE:
<223> OTHER INFORMATION: Description of Artificial Sequence: Synthetic
     nucleotide sequence

<400> SEQUENCE: 38

```
cagtctgtgc tgactcagcc accctcagcg tctgggaccc ccgggcagag ggtcaccatc       60
tcctgctctg gaagcagctc cagcattggg aataattttg tatcctggta tcagcagctc     120
ccaggaacgg cccccaaact cctcatctat gacaataata gcgaccctc agggqtccct     180 gaccgattct ctggctccaa gtctggcacc tcagcctccc tggccatcag tgggctccgg     240
tccgaggatg aggctgatta ttactgtgca gcatgggatg acagcctgaa tggttgggtg    300
ttcggcggag gaaccaagct gacggtccta ggt                                  333
```

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 39

Phe Leu Asp Thr Val Tyr Gly Asn Cys Ser Thr His Phe Thr Val Lys
 1               5                  10                  15
Thr Arg Lys Gly
            20

<210> SEQ ID NO 40
<211> LENGTH: 20
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 40

Pro Gln Cys Ser Thr His Ile Leu Gln Trp Leu Lys Arg Val His Ala
 1               5                  10                  15

Asn Pro Leu Leu
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Ile Ser Ile Pro Arg Leu Gln Ala Glu Ala Arg Ser Glu Ile Leu
 1               5                  10                  15

Ala His Trp Ser
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Leu Val Lys Glu Ala Leu Lys Glu Ser Gln Leu Pro Thr Val Met
 1               5                  10                  15

Asp Phe Arg Lys
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Lys Phe Val Thr Gln Ala Glu Gly Ala Lys Gln Thr Glu Ala Thr
 1               5                  10                  15

Met Thr Phe Lys
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Gly Ser Leu Arg His Lys Phe Leu Asp Ser Asn Ile Lys Phe Ser
 1               5                  10                  15

His Val Glu Lys
```

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Gly Thr Tyr Gly Leu Ser Cys Gln Arg Asp Pro Asn Thr Gly Arg
 1               5                  10                  15

Leu Asn Gly Glu
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Leu Asn Gly Glu Ser Asn Leu Arg Phe Asn Ser Ser Tyr Leu Gln
 1               5                  10                  15

Gly Thr Asn Gln
            20

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Leu Thr Ser Thr Ser Asp Leu Gln Ser Gly Ile Ile Lys Asn Thr
 1               5                  10                  15

Ala Ser Leu Lys
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ala Ser Leu Lys Tyr Glu Asn Tyr Glu Leu Thr Leu Lys Ser Asp
 1               5                  10                  15

Thr Asn Gly Lys
            20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 49

Asp Met Thr Phe Ser Lys Gln Asn Ala Leu Leu Arg Ser Glu Tyr Gln
 1               5                  10                  15

Ala Asp Tyr Glu
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Lys Val Lys Ile Ile Arg Thr Ile Asp Gln Met Gln Asn Ser Glu
 1               5                  10                  15

Leu Gln Trp Pro
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Ala Leu Asp Asp Ala Lys Ile Asn Phe Asn Glu Lys Leu Ser Gln
 1               5                  10                  15

Leu Gln Thr Tyr
            20

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Thr Thr Lys Gln Ser Phe Asp Leu Ser Val Lys Ala Gln Tyr Lys
 1               5                  10                  15

Lys Asn Lys His
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Glu Glu Met Leu Glu Asn Val Ser Leu Val Cys Pro Lys Asp Ala
 1               5                  10                  15

Thr Arg Phe Lys
            20

<210> SEQ ID NO 54
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Thr Ser His His Leu Val Ser Arg Lys Ser Ile Ser Ala Ala
 1               5                  10                  15

Leu Glu His Lys
            20

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Glu Asn Ile Asp Phe Asn Lys Ser Gly Ser Ser Thr Ala Ser Trp
 1               5                  10                  15

Ile Gln Asn Val
            20

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Arg Glu Val Thr Gln Arg Leu Asn Gly Glu Ile Gln Ala Leu Glu
 1               5                  10                  15

Leu Pro Gln Lys
            20

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Val Asp Val Leu Thr Lys Tyr Ser Gln Pro Glu Asp Ser Leu Ile
 1               5                  10                  15

Pro Phe Phe Glu
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Thr Phe Leu Ile Tyr Ile Thr Glu Leu Leu Lys Lys Leu Gln Ser
 1               5                  10                  15
```

Thr Thr Val Met
          20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Leu Asp Ile Ala Asn Tyr Leu Met Glu Gln Ile Gln Asp Asp Cys
 1               5                  10                  15

Thr Gly Asp Glu
          20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Thr Gly Asp Glu Asp Tyr Thr Tyr Lys Ile Lys Arg Val Ile Gly
 1               5                  10                  15

Asn Met Gly Gln
          20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Asn Met Gly Gln Thr Met Glu Gln Leu Thr Pro Glu Leu Lys Ser
 1               5                  10                  15

Ser Ile Leu Lys
          20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Ser Ile Leu Lys Cys Val Gln Ser Thr Lys Pro Ser Leu Met Ile
 1               5                  10                  15

Gln Lys Ala Ala
          20

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 63

Ile Gln Lys Ala Ala Ile Gln Ala Leu Arg Lys Met Glu Pro Lys Asp
 1               5                  10                  15
Lys Asp Gln Glu
            20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Leu Asn Gly Glu Ser Asn Leu Arg Phe Asn Ser Ser Tyr Leu Gln
 1               5                  10                  15
Gly Thr Asn Gln
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Leu Asn Ser His Gly Leu Glu Leu Asn Ala Asp Ile Leu Gly Thr
 1               5                  10                  15
Asp Lys Ile Asn
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Ile Gln Asn Val Asp Thr Lys Tyr Gln Ile Arg Ile Gln Ile Gln
 1               5                  10                  15
Glu Lys Leu Gln
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Tyr Ile Ser Asp Trp Trp Thr Leu Ala Ala Lys Asn Leu Thr Asp
 1               5                  10                  15
Phe Ala Glu Gln
            20

<210> SEQ ID NO 68
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Ala Thr Leu Gln Arg Ile Tyr Ser Leu Trp Glu His Ser Thr Lys
 1               5                  10                  15

Asn His Leu Gln
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Leu Leu Val Pro Pro Glu Thr Glu Glu Ala Lys Gln Val Leu Phe
 1               5                  10                  15

Leu Asp Thr Val
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Glu Ile Gly Leu Glu Gly Lys Gly Phe Glu Pro Thr Leu Glu Ala
 1               5                  10                  15

Leu Phe Gly Lys
            20

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Gly Ala Ser Met Lys Leu Thr Thr Asn Gly Arg Phe Arg Glu His
 1               5                  10                  15

Asn Ala Lys Phe
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Leu Ile Gly Asp Phe Glu Val Ala Glu Lys Ile Asn Ala Phe Arg
 1               5                  10                  15
```

Ala Lys Val His
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly His Ser Val Leu Thr Ala Lys Gly Met Ala Leu Phe Gly Glu Gly
 1               5                  10                  15

Lys Ala Glu Phe
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Lys Ser Ser Val Ile Thr Leu Asn Thr Asn Ala Glu Leu Phe Asn
 1               5                  10                  15

Gln Ser Asp Ile
            20

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Pro Asp Leu Gly Gln Glu Val Ala Leu Asn Ala Asn Thr Lys Asn
 1               5                  10                  15

Gln Lys Ile Arg
            20

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cccagtcacg acgttgtaaa acg                                        23

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77

-continued

```
gaaacagcta tgaaatacct attgc                                        25

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caggaaacag ctatgac                                                 17

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
agacccaagc tagcttggta c                                            21
```

PEPTIDE-BASED PASSIVE IMMUNIZATION THERAPY FOR TREATMENT OF ATHEROSCLEROSIS

TECHNICAL FIELD

The present invention relates to new isolated human antibodies raised against peptides being derivatives of apolipoprotein B, in particular antibodies to be used for immunization therapy for treatment of atherosclerosis, method for their preparation, and method for passive immunization using said antibodies.

In particular the invention includes:

The use of any isolated antibody raised against an oxidized form of the peptides listed in table 1, in particular MDA-modified peptides, preferably together with a suitable carrier and adjuvant as an immunotherapy or "anti-atherosclerosis "vaccine" for prevention and treatment of ischemic cardiovascular disease.

BACKGROUND OF THE INVENTION

The protective effects of humoral immunity are known to be mediated by a family of structurally related glycoproteins called antibodies. Antibodies initiate their biological activity by binding to antigens. Antibody binding to antigens is generally specific for one antigen and the binding is usually of high affinity. Antibodies are produced by B-lymphocytes. Blood contains many different antibodies, each derived from a clone of B-cells and each having a distinct structure and specificity for antigen. Antibodies are present on the surface of B-lymphocytes, in the plasma, in interstitial fluid of the tissues and in secretory fluids such as saliva and mucous on mucosal surfaces.

All antibodies are similar in their overall structure, accounting for certain similarities in physico-chemical features such as charge and solubility. All antibodies have a common core structure of two identical light chains, each about 24 kilo Daltons, and two identical heavy chains of about 55-70 kilo Daltons each. One light chain is attached to each heavy chain, and the two heavy chains are attached to each other. Both the light and heavy chains contain a series of repeating homologous units, each of about 110 amino acid residues in length which fold independently in a common globular motif, called an immunoglobulin (Ig) domain. The region of an antibody formed by the association of the two heavy chains is hydrophobic. Antibodies, and especially monoclonal antibodies, are known to cleave at the site where the light chain attaches to the heavy chain when they are subjected to adverse physical or chemical conditions. Because antibodies contain numerous cysteine residues, they have many cysteine-cysteine disulfide bonds. All Ig domains contain two layers of beta-pleated sheets with three or four strands of anti-parallel polypeptide chains.

Despite their overall similarity, antibody molecules can be divided into a small number of distinct classes and subclasses based on physicochemical characteristics such as size, charge and solubility, and on their behavior in binding to antigens. In humans, the classes of antibody molecules are: IgA, IgD, IgE, IgG and IgM. Members of each class are said to be of the same isotype. IgA and IgG isotypes are further subdivided into subtypes called IgA1, IgA2 and IgG1, IgG2, IgG3 and IgG4. The heavy chains of all antibodies in an isotype share extensive regions of amino acid sequence identity, but differ from antibodies belonging to other isotypes or subtypes. Heavy chains are designated by the letters of the Greek alphabet corresponding to the overall isotype of the antibody, e.g., IgA contains alpha., IgD contains delta., IgE contains epsilon., IgG contains .gamma., and IgM contains .mu. heavy chains. IgG, IgE and IgD circulate as monomers, whereas secreted forms of IgA and IgM are dimers or pentamers, respectively, stabilized by the J chain. Some IgA molecules exist as monomers or trimers.

There are between $10^8$ and $10^{10}$ structurally different antibody molecules in every individual, each with a unique amino acid sequence in their antigen combining sites. Sequence diversity in antibodies is predominantly found in three short stretches within the amino terminal domains of the heavy and light chains called variable (V) regions, to distinguish them from the more conserved constant (C) regions.

Atherosclerosis is a chronic disease that causes a thickening of the innermost layer (the intima) of large and medium-sized arteries. It decreases blood flow and may cause ischemia and tissue destruction in organs supplied by the affected vessel. Atherosclerosis is the major cause of cardiovascular disease including myocardial infarction, stroke and peripheral artery disease. It is the major cause of death in the western world and is predicted to become the leading cause of death in the entire world within two decades.

The disease is initiated by accumulation of lipoproteins, primarily low-density lipoprotein (LDL), in the extracellular matrix of the vessel. These LDL particles aggregate and undergo oxidative modification. Oxidized LDL is toxic and cause vascular injury. Atherosclerosis represents in many respects a response to this injury including inflammation and fibrosis.

In 1989 Palinski and coworkers identified circulating autoantibodies against oxidized LDL in humans. This observation suggested that atherosclerosis may be an autoimmune disease caused by immune reactions against oxidized lipoproteins. At this time several laboratories began searching for associations between antibody titers against oxidized LDL and cardiovascular disease. However, the picture that emerged from these studies was far from clear. Antibodies existed against a large number of different epitopes in oxidized LDL, but the structure of these epitopes was unknown. The term "oxidized LDL antibodies" thus referred to an unknown mixture of different antibodies rather than to one specific antibody. T cell-independent IgM antibodies were more frequent than T-cell dependent IgG antibodies.

Antibodies against oxidized LDL were present in both patients with cardiovascular disease and in healthy controls. Although some early studies reported associations between oxidized LDL antibody titers and cardiovascular disease, others were unable to find such associations. A major weakness of these studies was that the ELISA tests used to determine antibody titers used oxidized LDL particles as ligand. LDL composition is different in different individuals, the degree of oxidative modification is difficult both to control and assess and levels of antibodies against the different epitopes in the oxidized LDL particles can not be determined. To some extent, due to the technical problems it has been difficult to evaluate the role of antibody responses against oxidized LDL using the techniques available so far, but, however, it is not possible to create well defined and reproducable components of a vaccine if one should use intact oxidized LDL particles.

Another way to investigate the possibility that autoimmune reactions against oxidized LDL in the vascular wall play a key role in the development of atherosclerosis is to immunize animals against its own oxidized LDL. The idea behind this approach is that if autoimmune reactions against oxidized LDL are reinforced using classical immunization techniques this would result in increased vascular inflammation and progressive of atherosclerosis. To test this hypothesis rabbits were immunized with homologous oxidized LDL and then induced atherosclerosis by feeding the animals a high-cholesterol diet for 3 months.

However, in contrast to the original hypothesis immunization with oxidized LDL had a protective effect reducing atherosclerosis with about 50%. Similar results were also obtained in a subsequent study in which the high-cholesterol diet was combined with vascular balloon-injury to produce a more aggressive plaque development. In parallel with our studies several other laboratories reported similar observations. Taken together the available data clearly demonstrates that there exist immune reactions that protect against the development of atherosclerosis and that these involves autoimmunity against oxidized LDL.

These observations also suggest the possibility of developing an immune therapy or "vaccine" for treatment of atherosclerosis-based cardiovascular disease in man. One approach to do this would be to immunize an individual with his own LDL after it has been oxidized by exposure to for example copper. However, this approach is complicated by the fact that it is not known which structure in oxidized LDL that is responsible for inducing the protective immunity and if oxidized LDL also may contain epitopes that may give rise to adverse immune reactions.

The identification of epitopes in oxidized LDL is important for several aspects:

First, one or several of these epitopes are likely to be responsible for activating the anti-atherogenic immune response observed in animals immunized with oxidized LDL. Peptides containing these epitopes may therefore represent a possibility for development of an immune therapy or "atherosclerosis vaccine" in man. Further, they can be used for therapeutic treatment of atheroschlerosis developed in man.

Secondly, peptides containing the identified epitopes can be used to develop ELISAs able to detect antibodies against specific structure in oxidized LDL. Such ELISAs would be more precise and reliable than ones presently available using oxidized LDL particles as antigen. It would also allow the analyses of immune responses against different epitopes in oxidized LDL associated with cardiovascular disease.

U.S. Pat. No. 5,972,890 relates to a use of peptides for diagnosing atherosclerosis. The technique presented in said U.S. patent is as a principle a form of radiophysical diagnosis. A peptide sequence is radioactively labelled and is injected into the bloodstream. If this peptide sequence should be identical with sequences present in apolipoprotein B it will bind to the tissue where there are receptors present for apolipoprotein B. In vessels this is above all atherosclerotic plaque. The concentration of radioactivity in the wall of the vessel can then be determined e.g., by means of a gamma camera. The technique is thus a radiophysical diagnostic method based on that radioactively labelled peptide sequences will bound to their normal tissue receptors present in atherosclerotic plaque and are detected using an external radioactivity analysis. It is a direct analysis method to identify atherosclerotic plaque. It requires that the patient be given radioactive compounds.

Published studies (Palinski et al., 1995, and George et al., 1998) have shown that immunisation against oxidised LDL reduces the development of atherosclerosis. This would indicate that immuno reactions against oxidised LDL in general have a protecting effect. The results given herein have, however, surprisingly shown that this is not always the case. E.g., immunisation using a mixture of peptides #10, 45, 154, 199, and 240 gave rise to an increase of the development of atherosclerosis. Immunisation using other peptide sequences, e.g., peptide sequences #1, and 30 to 34 lacks total effect on the development of atherosclerosis. The results are surprising because they provide basis for the fact that immuno reactions against oxidised LDL, can protect against the development, contribute to the development of atherosclerosis, and be without any effect at all depending on which structures in oxidised LDL they are directed to. These findings make it possible to develop immunisation methods, which isolate the activation of protecting immuno reactions. Further, they show that immunisation using intact oxidised LDL could have a detrimental effect if the particles used contain a high level of structures that give rise to atherogenic immuno reactions.

The technique of the present invention is based on quite different principles and methods. In accordance with claim 1 the invention relates to antibodies raised against oxidized fragments of apolipoprotein B, which antibodies are used for immunisation against cardiovascular disease.

As an alternative to active immunisation, using the identified peptides described above, passive immunisation with pre-made antibodies directed to the same peptides is an attractive possibility. Such antibodies may be given desired properties concerning e.g. specificity and crossreactivity, isotype, affinity and plasma halflife. The possibility to develop antibodies with predetermined properties became apparent already with the advent of the monoclonal antibody technology (Milstein and Köhler, 1975 Nature, 256:495-7). This technology used murine hybridoma cells producing large amounts of identical, but murine, antibodies. In fact, a large number of preclinical, and also clinical trials were started using murine monoclonal antibodies for treatment of e.g. cancers. However, due to the fact that the antibodies were of non-human origin the immune system of the patients recognised them as foreign and developed antibodies to them. As a consequence the efficacy and plasma half-lives of the murine antibodies were decreased, and often side effects from allergic reactions, caused by the foreign antibody, prevented successful treatment.

To solve these problems several approaches to reduce the murine component of the specific and potentially therapeutic antibody were taken. The first approach comprised technology to make so called chimearic antibodies where the murine variable domains of the antibody were transferred to human constant regions resulting in an antibody that was mainly human (Neuberger et al. 1985, Nature 314:268-70). A further refinement of this approach was to develop humanised antibodies where the regions of the murine antibody that contacted the antigen, the so called Complementarity Determining Regions (CDRs) were transferred to a human antibody framework. Such antibodies are almost completely human and seldom cause any harmful antibody responses when administered to patients. Several chimearic or humanised antibodies have been registered as therapeutic drugs and are now widely used within various indications (Borrebaeck and Carlsson, 2001, Curr. Opin. Pharmacol. 1:404-408).

Today also completely human antibodies may be produced using recombinant technologies. Typically large libraries comprising billions of different antibodies are used. In contrast to the previous technologies employing chimearisation or humanisation of e.g. murine antibodies this technology does not rely on immunisation of animals to generate the specific antibody. In stead the recombinant libraries comprise a huge number of pre-made antibody variants why it is likely that the library will have at least one antibody specific for any antigen. Thus, using such libraries the problem becomes the one to find the specific binder already existing in the library, and not to generate it through immunisations. In order to find the good binder in a library in an efficient manner, various systems where phenotype i.e. the antibody or antibody fragment is linked to its genotype i.e. the encoding gene have been devised. The most commonly used such system is the so called phage display system where antibody fragments are expressed, displayed, as fusions with phage coat proteins on the surface of filamentous phage particles, while simultaneously carrying the genetic information encoding the displayed molecule (McCafferty et al., 1990, Nature 348:552-554). Phage displaying antibody fragments specific for a particular antigen may be selected through binding to the antigen in question. Isolated phage may then be amplified and the gene encoding the selected antibody variable domains may optionally be transferred to other antibody formats as e.g. full length immunoglobulin and expressed in high amounts using appropriate vectors and host cells well known in the art.

The format of displayed antibody specificities on phage particles may differ. The most commonly used formats are Fab (Griffiths et al., 1994. EMBO J. 13:3245-3260) and single chain (scFv) (Hoogenboom et al., 1992, J Mol Biol. 227:381-388) both comprising the variable antigen binding domains of antibodies. The single chain format is composed of a variable heavy domain (VH) linked to a variable light domain (VL) via a flexible linker (U.S. Pat. No. 4,946,778). Before use as analytical reagents, or therapeutic agents, the displayed antibody specificity is transferred to a soluble format e.g. Fab or scFv and analysed as such. In later steps the antibody fragment identified to have desireable characteristics may be transferred into yet other formats such as full length antibodies.

Recently a novel technology for generation of variability in antibody libraries was presented (WO98/32845, Soderlind et al., 2000, Nature BioTechnol. 18:852-856).

Antibody fragments derived from this library all have the same framework regions and only differ in their CDRs. Since the framework regions are of germline sequence the immunogenicity of antibodies derived from the library, or similar libraries produced using the same technology, are expected to be particularly low (Soderlind et al., 2000, Nature BioTechnol. 18:852-856). This property is expected to be of great value for therapeutic antibodies reducing the risk for the patient to form antibodies to the administered antibody thereby reducing risks for allergic reactions, the occurrence of blocking antibodies, and allowing a long plasma half-life of the antibody. Several antibodies derived from recombinant libraries have now reached into the clinic and are expected to provide therapeutic drugs in the near future.

Thus, when met with the challenge to develop therapeutic antibodies to be used in humans the art teaches away from the earlier hybridoma technology and towards use of modern recombinant library technology (Soderlind et al., 2001, Comb. Chem. & High Throughput Screen. 4:409-416). It was realised that the peptides identified (PCT/SE02/00679), and being a integral part of this invention, could be used as antigens for generation of fully human antibodies with predetermined properties. In contrast to earlier art (U.S. Pat. No. 6,225,070) the antigenic structures i.e. the peptides used in the present invention were identified as being particularly relevant as target sequences for therapeutic antibodies (PCT/SE02/00679). Also, in the present invention the antibodies are derived from antibody libraries omitting the need for immunisation of lipoprotein deficient mice to raise murine antibodies (U.S. Pat. No. 6,225,070). Moreover, the resulting antibodies are fully human and are not expected to generate any undesired immunological reaction when administered into patients.

The peptides used, and previously identified (PCT/SE02/00679) are the following:

TABLE 1

| A. High IgG, MDA-difference | | |
|---|---|---|
| P 11. | FLDTVYGNCSTHFTVKTRKG | (SEQ ID NO: 39) |
| P 25. | PQCSTHILQWLKRVHANPLL | (SEQ ID NO: 40) |
| P 74. | VISIPRLQAEARSEILAHWS | (SEQ ID NO: 41) |
| B. High IgM, no MDA-difference | | |
| P 40. | KLVKEALKESQLPTVMDFRK | (SEQ ID NO: 42) |
| P 68. | LKFVTQAEGAKQTEATMTFK | (SEQ ID NO: 43) |
| P 94. | DGSLRHKFLDSNIKFSHVEK | (SEQ ID NO: 44) |
| P 99. | KGTYGLSCQRDPNTGRLNGE | (SEQ ID NO: 45) |
| P 100. | RLNGESNLRFNSSYLQGTNQ | (SEQ ID NO: 46) |
| P 102. | SLTSTSDLQSGIIKNTASLK | (SEQ ID NO: 47) |
| P 103. | TASLKYENYELTLKSDTNGK | (SEQ ID NO: 48) |
| P 105. | DMTFSKQNALLRSEYQADYE | (SEQ ID NO: 49) |
| P 177. | MKVKIIRTIDQMQNSELQWP | (SEQ ID NO: 50) |
| C. High IgG, no MDA difference | | |
| P 143. | IALDDAKINFNEKLSQLQTY | (SEQ ID NO: 51) |
| P 210. | KTTKQSFDLSVKAQYKKNKH | (SEQ ID NO: 52) |
| D. NHS/AHP, IgG-ak > 2, MDA-difference | | |
| P 1. | EEEMLENVSLVCPKDATRFK | (SEQ ID NO: 53) |
| P 129. | GSTSHHLVSRKSISAALEHK | (SEQ ID NO: 54) |
| P 148. | IENIDFNKSGSSTASWIQNV | (SEQ ID NO: 55) |
| P 162. | IREVTQRLNGEIQALELPQK | (SEQ ID NO: 56) |
| P 252. | EVDVLTKYSQPEDSLIPFFE | (SEQ ID NO: 57) |
| E. NHS/AHP, IgM-ak > 2, MDA-difference | | |
| P 301. | HTFLIYITELLKKLQSTTVM | (SEQ ID NO: 58) |
| P 30. | LLDIANYLMEQIQDDCTGDE | (SEQ ID NO: 59) |
| P 31. | CTGDEDYTYKIKRVIGNMGQ | (SEQ ID NO: 60) |
| P 32. | GNMGQTMEQLTPELKSSILK | (SEQ ID NO: 61) |
| P 33. | SSILKCVQSTKPSLMIQKAA | (SEQ ID NO: 62) |
| P 34. | IQKAAIQALRKMEPKDKDQE | (SEQ ID NO: 63) |
| P 100. | RLNGESNLRFNSSYLQGTNQ | (SEQ ID NO: 64) |
| P 107. | SLNSHGLELNADILGTDKIN | (SEQ ID NO: 65) |
| P 149. | WIQNVDTKYQIRIQIQEKLQ | (SEQ ID NO: 66) |
| P 169. | TYISDWWTLAAKNLTDFAEQ | (SEQ ID NO: 67) |
| P 236. | EATLQRIYSLWEHSTKNHLQ | (SEQ ID NO: 68) |
| F. NHS/AHP, IgG-ak < 0.5, no MDA-difference | | |
| P 10. | ALLVPPETEEAKQVLFLDTV | (SEQ ID NO: 69) |
| P 45. | IEIGLEGKGFEPTLEALFGK | (SEQ ID NO: 70) |
| P 111. | SGASMKLTTNGRFREHNAKF | (SEQ ID NO: 71) |
| P 154. | NLIGDFEVAEKINAFRAKVH | (SEQ ID NO: 72) |

TABLE 1-continued

| P 199. | GHSVLTAKGMALFGEGKAEF | (SEQ ID NO: 73) |
| P 222. | FKSSVITLNTNAELFNQSDI | (SEQ ID NO: 74) |
| P 240. | FPDLGQEVALNANTKNQKIR | (SEQ ID NO: 75) | or an active site of one or more of these peptides.

In Table 1 above, the following is due:

(A) Fragments that produce high levels of IgG antibodies to MDA-modified peptides (n=3), (B) Fragments that produce high levels of IgM antibodies, but no difference between native and MDA-modified peptides (n=9), (C) Fragments that produce high levels of IgG antibodies, but no difference between native and MDA-modified peptides (n=2), (D) Fragments that produce high levels of IgG antibodies to MDA-modified peptides and at least twice as much antibodies in the NHP-pool as compared to the AHP-pool (n=5), (E) Fragments that produce high levels of IgM antibodies to MDA-modified peptides and at least twice as much antibodies in the NHP-pool as compared to the AHP-pool (n=11), and (F) Fragments that produce high levels of IgG antibodies, but no difference between intact and MDA-modified peptides but at least twice as much antibodies in the AHP-pool as compared to the NHP-pool (n=7).

SUMMARY OF THE INVENTION

The present invention relates to the use of at least one recombinant human antibody or an antibody fragment thereof directed towards at least one oxidized fragment of apolipoprotein B in the manufacture of a pharmaceutical composition for therapeutical or prophylactical treatment of atherosclerosis by means of passive immunization.

Further the invention relates to the recombinant preparation of such antibodies, as well as the invention relates to method for passive immunization using such antibodies raised using an oxidized apolipoprotein B fragment, as antigen, in particular a fragment as identified above.

The present invention utilises an isolated antibody fragment library to generate specific human antibody fragments against oxidized, in particular MDA modified peptides derived from Apo B100. Identified antibody fragments with desired characteristics may then rebuilt into full length human immunoglobulin to be used for therapeutic purposes.

BRIEF DESCRIPTION OF THE DRAWINGS

FIGS. 1A-1C are ELISA results from Screen II;
FIGS. 2A-2F are graphs of dose response for ELISAs;
FIG. 3 are the DNA sequences of various regions.

DETAILED DESCRIPTION OF THE INVENTION

Figures 4, 4A:
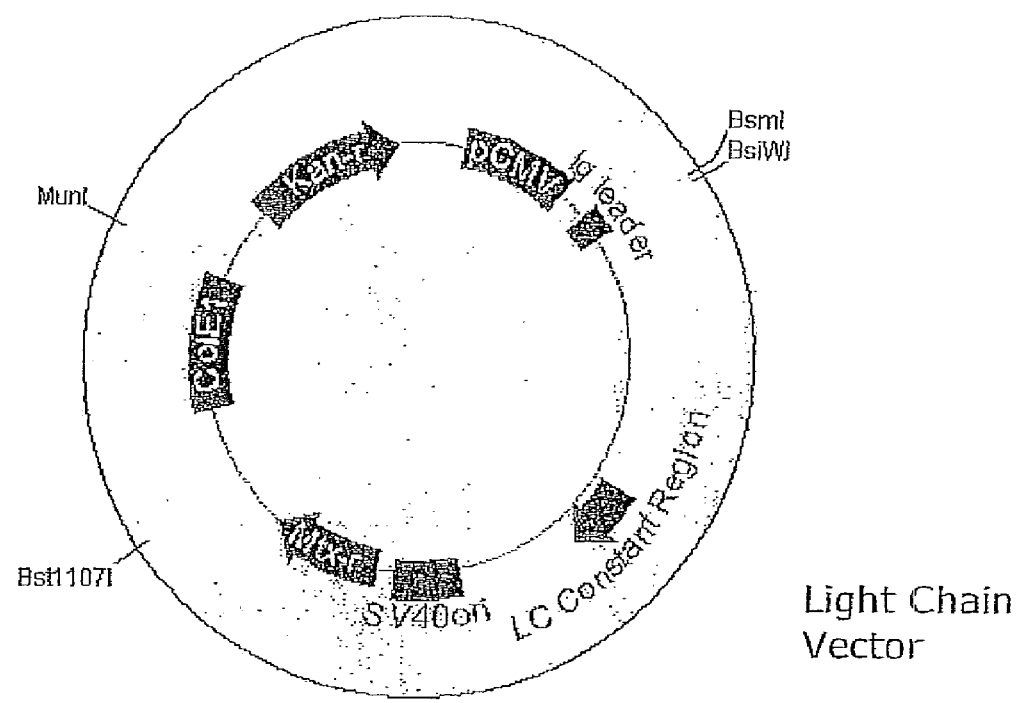
FIGS. 4A and 4B are light and heavy-chain vectors.
Figures 4, 4B:
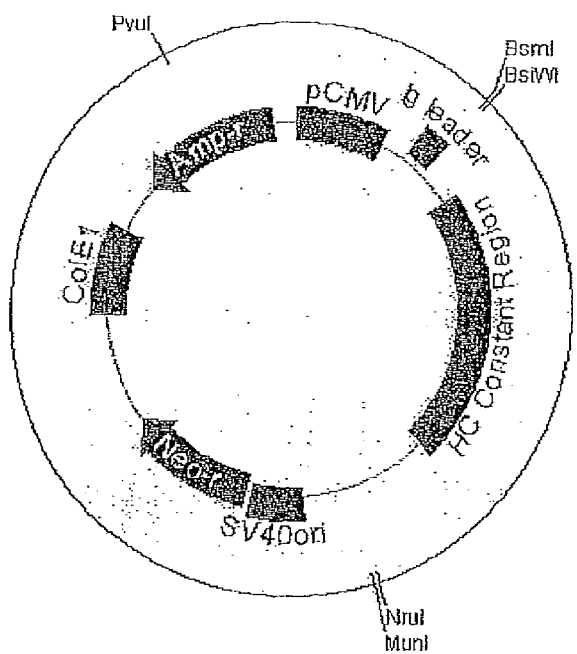

Below will follow a detailed description of the invention examplified by, but not limited to, human antibodies derived from an isolated antibody fragment library and directed towards two MDA modified peptides from ApoB 100.

EXAMPLE 1

Selection of scFv against MDA Modified Peptides
IEIGL EGKGF EPTLE ALFGK (SEQ ID NO: 70)
(P45, Table 1) and KTTKQ SFDLS VKAQY
KKNKH ) (SEQ ID NO: 52) (P210, Table 1)

The target antigens were chemically modified to carry Malone-di-aldehyde (MDA) groups on lysines and histidines. The modified peptides were denoted IEI (P45) and KTT (P210).

Selections were performed using BioInvent's n-CoDeR™ scFv library for which the principle of construction and production have been described in Soderlind et al. 2000, Nature BioTechnology. 18, 852-856. Briefly, CDRs are isolated from human immunoglobulin genes and are shuffled into a fixed framework. Thus variability in the resulting immunoglobulin variable regions is a consequence of recombination of all six CDRs into the fixed framework. The framework regions are all germline and are identical in all antibodies. Thus variability is restricted to the CDRs which are all natural and of human origin. The library contains approximately $2 \times 10^{10}$ independent clones and a 2000 fold excess of clones were used as input for each selection. Selections were performed in three rounds. In selection round 1, Immunotubes (NUNC maxisorb 444202) were coated with 1.2 ml of 20 µg/ml MDA-modified target peptides in PBS (137 mM NaCl, 2.7 mM KCl, 4.3 mM $Na_2HPO_4$, 1.4 mM $KH_2PO_4$) with end over end agitation at +4° C. over night. The tubes were then blocked with TPBSB5% (5% BSA, 0.05% Tween 20, 0.02% sodium Azide in PBS) for 30 minutes and washed twice with TPBSB3% (3% BSA, 0.05% Tween 20, 0.02% sodium Azide in PBS) before use. Each target tube was then incubated with approximately $2 \times 10^{13}$ CFU phages from the n-CodeR™ library in 1.8 ml TPBSB3% for 2 h at room temperature, using end over end agitation. The tubes were then washed with 15×3 ml TPBSB3% and 2×1 ml PBS before the bound phages were eluted with 1 ml/tube of 2 mg/ml trypsin (Roche, 109819) for 30 minutes at room temperature. This procedure takes advantage of a specific trypsin site in the scFv-fusion protein to release the phage from the target. The reaction was stopped by the addition of 100 µl of Aprotein (0.2 mg/ml, Roche, cat.236624), and the immunotubes were washed with 300 ul PBS, giving a final volume of 1.4 ml.

For amplification of the selected phage *E. Coli* HB101F' cells were grown exponentially in 10 ml of LB medium (Merck, cat. 1.10285) to $OD_{600}$ =0.5 and infected with the selected and eluted phage principally as described (Soderlind et al., 2000, Nature BioTechnol. 18, 852-856. The resulting phage supernatant was then precipitated by addition of 1/4 volume of 20% $PEG_{6000}$ in 2.5 M NaCl and incubated for 5 h at +4° C. The phages were then pelleted by centrifugation for 30 minutes, 13000×g, re-suspended in 500 µl PBS and used in selection round 2.

The amplified phagestock was used in selection round 2 in a final volume of 1.5 ml of 5% BSA, 0.05% Tween 20, 0.02% sodium Azide in PBS. Peptide without MDA modification ($4 \times 10^{-7}$ M) was also included for competition against binders to MDA-unmodified target peptide. The mixture was incubated in immunotubes prepared with antigen as described above, except that the tubes were blocked with 1% Casein instead of TPBSB3%. The incubations and washing of the immunotubes were as described for selection 1. Bound phages were then eluted for 30 minutes using 600 µl of 100 mM Tris-Glycine buffer, pH 2.2. The tubes were washed with additional 200 µl glycin buffer and the eluates were pooled and then neutralised with 96 µl of 1 M Tris-HCl, pH 8.0. The samples were re-natured for 1 h at room temperature and used for selection round 3.

For selection round 3, BSA, Tween 20 and Sodium Azide were added to the renaturated phage pool to a final concentration of 3%, 0.05% and 0.02%, respectively. Competitor peptides, MDA modified unrelated peptides as well as native target peptides without modification were added to a concentration of $1 \times 10^{-7}$ M. The phage mixtures (1100 µl) were added to immunotubes coated with target antigen as described in selection 1 and incubated over night at 4° C. with agitation. The tubes were then washed with 3×3 ml TPBSB 3%, 5×3 ml PBS and eventually bound phages were eluted using trypsin as described in selection round 1 above. Each eluate was infected to 10 ml of logarithmically growing HB101F' in LB containing 100 µg/ml ampicillin, 15 µg/ml tetracycline, 0.1% glucose, and grown over night at 30° C., 200 rpm in a shaker incubator.

The over night cultures were used for mini scale preparation of plasmid DNA, using Biorad mini prepp Kit (Cat. 732 6100). To remove the phage gene III part from the expression vector, 0.25 µg of the plasmid DNA was cut for 2 h at 37° C. using 2.5 U Eag-1 (New England Biolabs, cat. R050) in the buffer recommended by the supplier. The samples were then heat inactivated for 20 minutes at 65° C. and ligated over night at 16° C. using 1 U T4 DNA ligase in 30 µl of 1× ligase buffer (Gibco/BRL). This procedure will join two Eag-1 sites situated on opposite sides of the phage gene III fragment, thus creating a free scFv displaying a terminal 6× his tag. After ligation the material was digested for 2 h at 37° C. in a solution containing 30 ul ligation mix, 3.6 µl 10× REACT3 stock, 0.4 µl 1 M NaCl, 5 µl $H_2O_2$, in order to destroy clones in which the phage gene III segment had been religated. Twenty (20) ng of the final product were transformed into chemical competent Top10F' and spread on 500 cm² Q-tray LA-plates (100 µg/ml Amp, 1% glucose), to enable the picking of single colonies for further screening.

Screening of the n-CoDeR™ scFv Library for Specific Antibody Fragments Binding t0 MDA Modified Peptides from Apolipoprotein B-100

In order to identify scFv that could discriminate between MDA modified IEI (P45) peptide and native IEI and between MDA modified KTT (P210) and native KTT respectively screenings were performed on bacterial supernatants from selected scFv expressing clones.

Colony picking of single clones, expression of scFv and screening number 1 was performed on BioInvent's automatic system according to standard methods. 1088 and 831 single clones selected against the MDA modified IEI and KTT peptides respectively were picked and cultured and expressed in micro titre plates in 100 µl LB containing 100 µg ampicillin/ml.

For screening number 1 white Assay plates (Greiner 655074) were coated with 54 pmol peptide/well in coating buffer (0.1 M Sodium carbonate, pH 9.5), either with MDA modified peptide which served as positive target or with corresponding unmodified peptide which served as non target. In the ELISA the expressed scFv were detected through a myc-tag situated C-terminal to the scFv using 1 µg/ml of anti-c-myc monoclonal (9E10 Roche 1667 149) in wash buffer. As a secondary antibody Goat-anti-mouse alkaline phosphatase conjugate (Applied Biosystems Cat # AC32ML) was used at 25000 fold dilution. For luminescence detection CDP-Star Ready to use with Emerald II Tropix (Applied Biosystems Cat # MS100RY) were used according to suppliers recommendation.

ScFv clones that bound MDA modified peptide but not native peptide were re expressed as described above and to screening another time in a luminescent ELISA (Table 2 and FIG. 1). Tests were run both against directly coated peptides (108 pmol/well coated with PBS) and the more physiological target, LDL particles (1 µg/well coated in PBS+1 mM EDTA) containing the ApoB-100 protein with and without MDA modification were used as targets. Positive clones were those that bound oxidised LDL and MDA modified peptide but not native LDL or peptide. The ELISA was performed as above except that the anti-His antibody (MaBO50 RαD) was used as the detection antibody. Twelve IEI clones and 2 KTT clones were found to give more than three fold higher luminescence signal at 700 nm for the MDA modified form than for the native form both for the peptide and LDL.

The identified clones were further tested through titration against a fixed amount (1 µg/well) of MDA LDL and native LDL in order to evaluate the dose response of the scFv (FIG. 2).

TABLE 2

Screening results. The number of clones tested in each screening step for each target. The scored hits in percent are shown within brackets.

| | | Target | |
|---|---|---|---|
| | | IEI | KTT |
| Screening number 1 | Tested Clones | 1088 | 831 |
| | Scored Hits | 64 | 33 |
| | (%) | (5.9%) | (4.0%) |
| Screening number 2 | Tested Clones | 64 | 33 |
| | Scored Hits | 12 | 2 |
| | (%) | (1.1%) | (0.2%) |
| Dose response | Tested Clones | 12 | 2 |
| | Scored Hits | 8 | 2 |
| | (%) | (0.7%) | (0.2%) |

The sequences of the chosen scFv clones were determined in order to find unique clones. Bacterial PCR was performed with the Boeringer Mannheim Expand kit using primers (5'-CCC AGT CAC GAC GTT GTA AAA CG-3') (SEQ ID NO: 76) and (5'-GAA ACA GCT ATG AAA TAC CTA TTG C-3') (SEQ ID NO: 77) and a GeneAmp PCR system 9700 (PE Applied system) using the temperature cycling program 94° C. 5 min, 30 cycles of 94° C. 30 s, 52° C. for 30 s and 68° C. for 2 min and finally 5 min at 68 min. The sequencing reaction was performed with the bacterial PCR product (five fold diluted) as template, using Big Dye Terminator mix from PE Applied Biosystems and the GeneAmp PCR system 9700 (PE Applied system) and the temperature cycling program 25 cycles of 96° C. 10 s, 50° C. for 5 s and 60° C. for 4 min. The extension products were purified according to the supplier's instructions and the separation and detection of extension products was done by using a 3100 Genetic analyser (PE Applied Biosystems). The sequences were analysed by the in house computer program. From the sequence information homologous clones and clones with inappropriate restriction sites were excluded, leaving six clones for IgG conversion.

The DNA sequence of the variable heavy (VH) and variable light (VL) domains of the finally selected clones are shown in FIG. 3.

EXAMPLE 2

Transfer of Genes Encoding the Variable Parts of Selected scFv to Full Length Human IgG1 Vestors.

Bacteria containing scFv clones to be converted to Ig-format were grown over night in LB supplemented with 100 μg/ml ampicillin. Plasmid DNA was prepared from over night cultures using the Quantum Prep, plasmid miniprep kit from Biorad (# 732-6100). The DNA concentration was estimated by measuring absorbance at 260 nm, and the DNA was diluted to a concentration of 2 ng/μl. VH and VL from the different scFv-plasmids were PCR amplified in order to supply these segments with restriction sites compatible with the expression vectors (see below). 5' primers contain a BsmI and 3' primers contain a BsiWI restriction enzyme cleavage site (shown in italics). 3' primers also contained a splice donor site (shown in bold).

Primers for amplification of VH-segments:

```
                                         (SEQ. ID. NO: 13)
5'VH:    5'-GGTGTGCATTCCGAGGTGCAGCTGTTGGAG (SEQ. ID. NO: 14)
3'VH:    5'-GACGTACGACTCACCTGAGCTCACGGTGACCAG
```

Primers for amplification of VL-segments:

```
                                         (SEQ. ID. NO: 15)
5'VL:    5'-GGTGTGCATTCCCAGTCTGTGCTGACTCAG (SEQ. ID. NO: 16)
3'VL:    5'-GACGTACGTTCTACTCACCTAGGACCGTCAGCTT
```

PCR was conducted in a total volume of 50 μl, containing 10 ng template DNA, 0.4 μM 5' primer, 0.4 μM 3' primer and 0.6 mM dNTP (Roche, #1 969 064). The polymerase used was Expand long template PCR system (Roche # 1 759 060), 3.5 u per reaction, together with each of the supplied buffers in 3 separate reactions. Each PCR amplification cycle consisted of a denaturing step at 94° C. for 30 seconds, an annealing step at 55° C. for 30 seconds, and an elongating step at 68° C. for 1.5 minutes. This amplification cycle was repeated 25 times. Each reaction began with a single denaturing step at 94° C. for 2 minutes and ended with a single elongating step at 68° C. for 10 minutes. The existence of PCR product was checked by agarose gel electrophoresis, and reactions containing the same amplified material (from reactions with different buffers) were pooled. The PCR amplification products were subsequently purified by spin column chromatography using S400-HR columns (Amersham-Pharmacia Biotech # 27-5240-01).

Four (4) μl of from each pool of PCR products were used for TOPO TA cloning (pCR 2.1 TOPO, InVitrogen #K4550-01) according to the manufacturers recommendations. Bacterial colonies containing plasmids with inserts were grown over night in LB supplemented with 100 μg/ml ampicillin and 20 μg/ml kanamycin. Plasmid DNA was prepared from over night cultures using the Quantum Prep, plasmid miniprep kit from Biorad (# 732-6100). Plasmid preparations were purified by spin column chromatography using S400-HR columns (Amersham-Pharmacia Biotech # 27-5240-01). Three plasmids from each individual VH and VL cloning were subjected to sequence analysis using BigDye Cycle Sequencing (Perkin Elmer Applied Biosystem, # 4303150). The cycle sequencing program consisted of a denaturing step at 96° C. for 10 seconds, an annealing step at 50° C. for 15 seconds, and an elongating step at 60° C. for 4 minutes. This cycle was repeated 25 times. Each reaction began with a single denaturing step at 94° C. for 1 minute. The reactions were performed in a volume of 10 μl consisting of 1 μM primer (5'-CAGGAAACAGCTATGAC) (SEQ ID NO: 78), 3 μl plasmid DNA and 4 μl Big Dye reaction mix. The reactions were precipitated according to the manufacturers recommendations, and samples were run on a ABI PRISM 3100 Genetic Analyzer. Sequences were compared to the original scFv sequence using the alignment function of the OMIGA sequence analysis software (Oxford Molecular Ltd).

Plasmids containing VH and VL segments without mutations were restriction enzyme digested. To disrupt the pCR 2.1 TOPO vector, plasmids were initially digested with DraI (Roche # 1 417 983) at 37° C. for 2 hours. Digestions were heat inactivated at 70° C. for 20 minutes and purified by spin column chromatography using S400-HR columns (Amersham-Pharmacia Biotech # 27-5240-01). The purified DraI digestions were subsequently digested with BsmI (Roche # 1 292 307) and BsiWI (Roche # 1 388 959) at 55° C. over night. Digestions were purified using phenol extraction and precipitation. The precipitated DNA was dissolved in 10 μl H$_2$O and used for ligation.

The expression vectors were obtained from Lars Norderhaug (J. Immunol. Meth. 204 (1997) 77-87). After some modifications, the vectors (FIG. 4) contain a CMV promoter, an Ig-leader peptide, a cloning linker containing BsmI and BsiWI restriction sites for cloning of VH/VL, genomic constant regions of IgG1 (heavy chain (HC) vector) or lambda (light chain (LC) vector), neomycin (HC vector) or methotrexate (LC vector) resistance genes for selection in eukaryotic cells, SV40 and ColEI origins of replication and ampicillin (HC vector) or kanamycin (LC vector) resistance genes for selection in bacteria.

The HC and LC vectors were digested with BsmI and BsiWI, phosphatase treated and purified using phenol extraction and precipitation. Ligation were set up at 16° C. over night in a volume of 10 μl, containing 100 ng digested vector, 2 μl digested VH/VL-pCR 2.1 TOPO vector (see above), 1 U T4 DNA ligase (Life Technologies, # 15224-025) and the supplied buffer. 2 μl of the ligation mixture were subsequently transformed into 50 μl chemocompetent top10F' bacteria, and plated on selective (100 μg/ml ampicillin or 20 μg/ml kanamycin) agar plates.

Colonies containing HC/LC plasmids with VH/VL inserts were identified by colony PCR:

```
Forward primer:
5'-ATGGGTGACAATGACATC        (SEQ ID NO: 17)

Reverse primer:
5'-AAGCTTGCTAGCGTACG         (SEQ ID NO: 18)
```

PCR was conducted in a total volume of 20 μl, containing bacterias, 0.5 μM forward primer, 0.5 μM reverse primer and 0.5 mM dNTP (Roche, #1 969 064). The polymerase used was Expand long template PCR system (Roche # 1 759 060), 0.7 U per reaction, together with the supplied buffer #3. Each PCR amplification cycle consisted of a denaturing step at 94° C. for 30 seconds, an annealing step at 52° C. for 30 seconds, and an elongating step at 68° C. for 1.5 minutes. This amplification cycle was repeated 30 times. Each reaction began with a single denaturing step at 94° C. for 2 minutes and ended with a single elongating step at 68° C. for 5 minutes. The existence of PCR product was checked by agarose gel electrophoresis. Colonies containing HC/LC plasmids with VH/VL inserts were grown over night in LB supplemented with 100 μg/ml ampicillin or 20 μg/ml kanamycin. Plasmid DNA was prepared from over night cultures using the Quantum Prep, plasmid miniprep kit from Biorad (# 732-6100). Plasmid preparations were purified by spin column chromatography using S400-HR columns (Amersham-Pharmacia Biotech # 27-5240-01). To confirm the integrity of the DNA sequence, three plasmids from each individual VH and VL were subjected to sequence analysis using BigDye Cycle Sequencing (Perkin Elmer Applied Biosystem, # 4303150). The cycle sequencing program consisted of a denaturing step at 96° C. for 10 seconds, an annealing step at 50° C. for 15 seconds, and an elongating step at 60° C. for 4 minutes. This cycle was repeated 25 times. Each reaction began with a single denaturing step at 94° C. for 1 minute. The reactions were performed in a volume of 10 μl consisting of 1 μM primer (5'-AGACCCAAGCTAGCTTGGTAC) (SEQ ID NO: 79), 3 μl plasmid DNA and 4 μl Big Dye reaction mix. The reactions were precipitated according to the manufacturers recommendations, and samples were run on a ABI PRISM 3100 Genetic Analyzer. Sequences were analysed using the OMIGA sequence analysis software (Oxford Molecular Ltd). The plasmid DNA was used for transient transfection of COS-7 cells (see below) and were digested for production of a joined vector, containing heavy and light chain genes on the same plasmid.

Heavy and light chain vectors containing VH and VL segments originating from the same scFv were cleaved by restriction enzymes and ligated: HC- and LC-vectors were initially digested with MunI (Roche # 1 441 337) after which digestions were heat inactivated at 70° C. for 20 minutes and purified by spin column chromatography using S200-HR columns (Amersham-Pharmacia Biotech # 27-5120-01). HC-vector digestions were subsequently digested with NruI (Roche # 776 769) and LC-vector digestions with Bst1107I (Roche # 1 378 953). Digestions were then heat inactivated at 70° C. for 20 minutes and purified by spin column chromatography using S400-HR columns (Amersham-Pharmacia Biotech # 27-5240-01). 5 μl of each digested plasmid were ligated at 16° C. over night in a total volume of 20 μl, containing 2 U T4 DNA ligase (Life Technologies, # 15224-025) and the supplied buffer. 2 μl of the ligation mixture were subsequently transformed into 50 μl chemocompetent top10F' bacteria, and plated on selective (100 μg/ml ampicillin and 20 μg/ml kanamycin) agar plates.

Bacterial colonies were grown over night in LB supplemented with 100 μg/ml ampicillin and 20 μg/ml kanamycin. Plasmid DNA was prepared from over night cultures using the Quantum Prep, plasmid miniprep kit from Biorad (# 732-6100). Correctly joined vectors were identified by restriction enzyme digestion followed by analyses of fragment sizes by agarose gel-electrophoreses Plasmid preparations were purified by spin column chromatography using S400-HR columns (Amersham-Pharmacia Biotech # 27-5240-01) and used for transient transfection of COS-7 cells.

COS-7 cells (ATCC # CRL-1651) were cultured at 37° C. with 5% $CO_2$ in Dulbeccos MEM, high glucose+Glutamaxl (Invitrogen # 31966021), supplementd with 0.1 mM non-essential amino acids (Invitrogen # 11140035) and 10% fetal bovine sera (Invitrogen # 12476-024, batch # 1128016). The day before transfection, the cells were plated in 12-well plates (Nunc, # 150628) at a density of $1.5 \times 10^5$ cells per well.

Prior to transfection, the plasmid DNA was heated at 70° C. for 15 minutes. Cells were transfected with 1 μg HC-plasmid+1 μg LC-plasmid, or 2 μg joined plasmid per well, using Lipofectamine 2000 Reagent (Invitrogen, # 11668019) according to the manufacturers recommendations. 24 hours post transfection, cell culture media was changed and the cells were allowed to grow for 5 days. After that, medium was collected and protein production was assayed for using ELISA.

Ninetysix (96)-well plates (Costar # 9018, flat bottom, high binding) were coated at 4° C. over night by adding 100 μl/well rabbit anti-human lamda light chain antibody (DAKO, # A0193) diluted 4000 times in coatingbuffer (0.1M sodium carbonate, pH 9.5). Plates were washed 4 times in PBS containing 0.05% Tween 20 and thereafter blocked with 100 μl/well PBS+3% BSA (Albumin, fraction V, Roche # 735108) for 1 h. at room temperature. After washing as above, 100 μl/well of sample were added and incubated in room temperature for 1 hour. As a standard for estimation of concentration, human purified IgG1 (Sigma, # I5029) was used. Samples and standard were diluted in sample buffer (1× PBS containing 2% BSA and 0.5% rabbit serum (Sigma # R4505). Subsequently, plates were washed as described above and 100 μl/well of rabbit anti-human IgG (y-chain) HRP-conjugated antibody (DAKO, # P214) diluted 8000 times in sample buffer was added and incubated at room temperature for 1 hour. After washing 8 times with PBS containing 0.05% Tween 20, 100 μl/well of a substrate solution containing one OPD tablet (10 mg, Sigma # P8287,) dissolved in 15 ml citric acid buffer and 4.5 μl $H_2O_2$ (30%) was added. After 10 minutes, the reaction was terminated by adding 150 μl/well of 1M HCl. Absorbance was measured at 490-650 nm and data was analyzed using the Softmax software.

Bacteria containing correctly joined HC- and LC-vectors were grown over night in 500 ml LB supplemented with ampicillin and kanamycin. Plasmid DNA was prepared from over night cultures using the Quantum Prep, plasmid maxiprep kit from Biorad (# 732-6130). Vectors were linearized using PvuI restriction enzyme (Roche # 650 129). Prior to transfection, the linearized DNA was purified by spin column chromatography using S400-HR columns (Amersham-Pharmacia Biotech # 27-5240-01) and heated at 70° C for 15 minutes.

EXAMPLE 3

Stable Transfection of NSO Cells Expressing Antibodies against MDA Modified Peptides from Apolipoprotein B-100.

NSO cells (ECACC no. 85110503) were cultured in DMEM (cat nr 31966-021, Invitrogen) supplemented with 10% Fetal Bovine Serum (cat no. 12476-024, lot: 1128016, Invitrogen) and 1× NEAA (non-essential amino acids, cat no. 11140-053, Invitrogen). Cell cultures are maintained at 37° C. with 5% $CO_2$ in humidified environment.

DNA constructs to be transfected were four constructs of IEI specific antibodies (IEI-A8, IEI-D8, IEI-E3, IEI-G8), two of KTT specific antibodies (KTT-B8, KTT-D6) and one control antibody (JFPA12).The day before transfection, the cells were trypsinized and counted, before plating them in a T-75 flask at $12 \times 10^6$ cells/flask. On the day of transfection, when the cells were 85-90% confluent, the cells were plated in 15 ml DMEM+1× NEAA+10% FBS (as above). For each flask of cells to be transfected, 35-40 μg of DNA were diluted into 1.9 ml of OPTI-MEM I Reduced Serum Medium (Cat no. 51985-026, lot: 3062314, Invitrogen) without serum. For each flask of cells, 114 µl of Lipofectamine 2000 Reagent (Cat nr. 11668-019, lot: 1116546, Invitrogen) were diluted into 1.9 ml OPTI-MEM I Reduced Serum Medium in another tube and incubated for 5 min at room temperature. The diluted DNA was combined with the diluted Lipofectamine 2000 Reagent (within 30 min) and incubated at room temperature for 20 min to allow DNA-LF2000 Reagent complexes to form.

The cells were washed with medium once and 11 ml DMEM+1+ NEAA+10% FBS were added. The DNA-LF2000 Reagent complexes (3.8 ml) were then added directly to each flask and gently mixed by rocking the flask back and forth. The cells were incubated at 37° C. in a 5% $CO_2$ incubator for 24 h.

The cells were then trypsinized and counted, and subsequently plated in 96-well plates at $2 \times 10^4$ cells/well using five 96-well plates/construct. Cells were plated in 100 µl well of DMEM+1× NEAA+10% FBS (as above) containing G418-sulphate (cat nr. 10131-027, lot: 3066651, Invitrogen) at 600 µg/ml. The selection pressure was kept unchanged until harvest of the cells.

The cells were grown for 12 days and assayed for antibody production using ELISA. From each construct cells from the 24 wells containing the highest amounts of IgG were transferred to 24-well plates and were allowed to reach confluency. The antibody production from cells in these wells was then assayed with ELISA and 5-21 pools/construct were selected for re-screening (Table 3). Finally cells from the best 1-4 wells for each construct were chosen. These cells were expanded successively in cell culture flasks and finally transferred into triple layer flasks (500 cm2) in 200 ml of (DMEM+1× NEAA+10% Ultra low IgG FBS (cat.no. 16250-078, lot.no. 113466, Invitrogen)+G418 (600 µg/ml)) for antibody production. The cells were incubated for 7-10 days and the supernatants were assayed by ELISA, harvested and sterile filtered for purification.

EXAMPLE 4

Production and Purification of Human IgG1

Supernatants from NSO cells transfected with the different IgG1 antibodies were sterile filtered using a 0.22 µm filter and purified using an affinity medium MabSelect™ with recombinant protein A, (Cat. No. 17519901 Amersham Biosciences).

Bound human IgG1 was eluted with HCL-glycine buffer pH 2.8. The eluate was collected in 0.5 ml fractions and $OD_{280}$ was used to determine presence of protein. The peak fractions were pooled and absorbance was measured at 280 nm and 320 nm. Buffer was changed through dialysis against a large volume of PBS. The presence of endotoxins in the purified IgG-1 preparations was tested using a LAL test (QCL-1000$^R$, cat. No. 50-647U Bio Whittaker). The samples contained between 1 and 12 EU/ml endotoxin. The purity of the preparations were estimated to exceed 98% by PAGE analysis.

TABLE 3

Summary of Production and Purification of human IgG1

| Clone name | Volume culture supernatant (ml) | Total IgG1 in supernatant (mg) | Total IgG1 Purified (mg) | Yield (%) |
|---|---|---|---|---|
| IEI-A8 | 600 | 68 | 42 | 61.8 |
| IEI-D8 | 700 | 45 | 21 | 46.7 |
| IEI-E3 | 700 | 44.9 | 25.6 | 60 |
| IEI-G8 | 600 | 74 | 42.4 | 57.3 |
| KTT-B8 | 1790 | 77.3 | 37.6 | 48.6 |
| KTT-D6 | 1845 | 47.8 | 31.8 | 66.5 |
| JFPA12 | 2000 | 32.2 | 19.2 | 59.6 |

Figure 5:
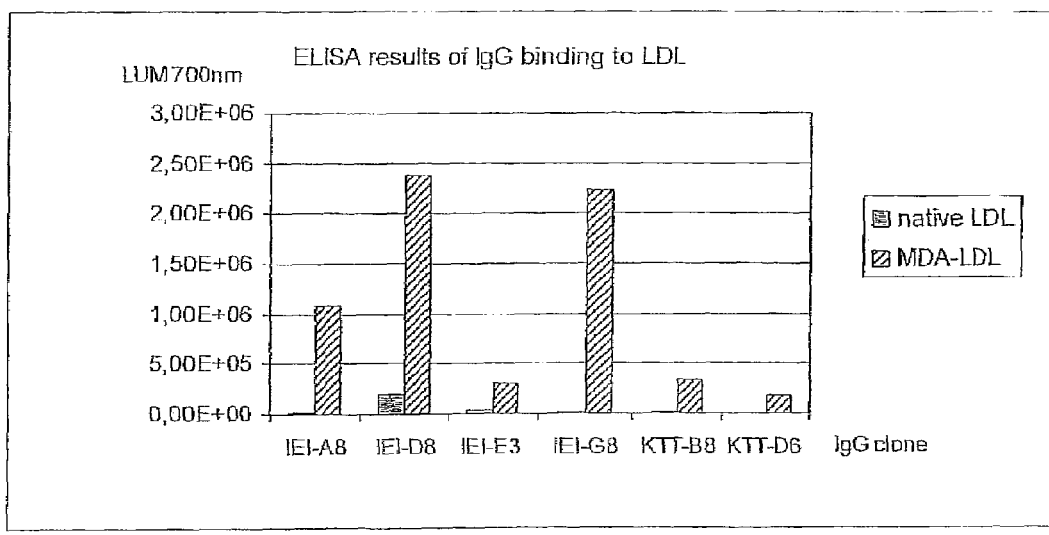
FIG. 5 is a graph of ELISA results.

The purified IgG1 preparations were tested in ELISA for reactivity to MDA modified and un-modified peptides (FIG. 5) and were then used in functional in vitro and in vivo studies.

EXAMPLE 5

Analysis of Possible Anti-Atherogenic Effect of Antibodies Are Performed Both in Experimental Animals and in Cell Culture Studies.

1. Effect of antibodies on atherosclerosis in apolipoprotein E knockout (apo E-) mice. Five weeks old apo E- mice are fed a cholesterol-rich diet for 15 weeks. This treatment is known to produce a significant amount of atherosclerotic plaques in the aorta and carotid arteries. The mice are then given an intraperitoneal injection containing 500 µg of the respective antibody identified above. Control mice are given 500 µg of an irrelevant control antibody or PBS alone. Treatments are repeated after 1 and 2 weeks. The mice are sacrificed 4 weeks after the initial antibody injection. The severity of atherosclerosis in the aorta is determined by Oil Red O staining of flat preparations and by determining the size of subvalvular atherosclerotic plaques. Collagen, macrophage and T cell content of subvalvular atherosclerotic plaques is determined by Masson trichrome staining and cell-specific immunohistochemistry. Quantification of Oil Red O staining, the size of the subvalvular plaques, trichrome staining and immunohistochemical staining is done using computer-based image analysis.

Figure 6:
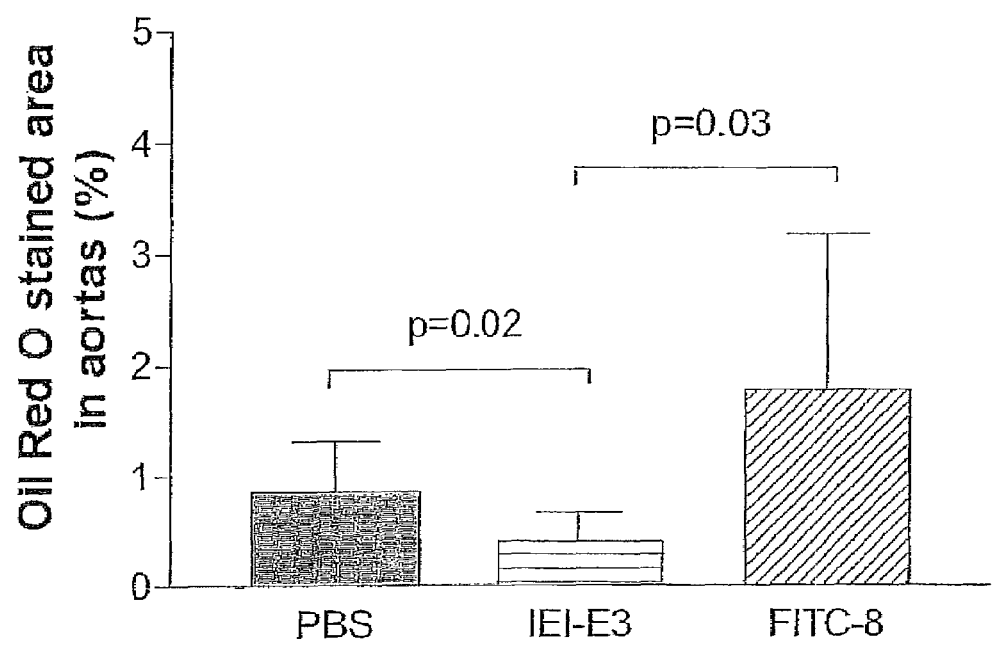
FIG. 6 is a graph of Oil Red O Stained area in aortas.

In a first experiment the effect of the antibodies on development of atherosclerosis was analysed in apo E−/− mice fed a high-cholesterol diet. The mice were given three intraperitoneal injections of 0.5 mg antibody with week intervals starting at 21 weeks of age, using PBS as control. They were sacrificed two weeks after the last antibody injection, and the extent of atherosclerosis was assessed by Oil Red O staining of descending aorta flat preparations. A pronounced effect was observed in mice treated with the IEI-E3 antibody, with more than 50% reduction of atherosclerosis as compared to the PBS group (P=0.02) and to a control group receiving a human IgG1 antibody (FITC8) directed against a non-relevant fluorescein isothiocynate (FITC) antigen (P=0.03) (FIG. 6). The mice tolerated the human antibodies well and no effects on the general health status of the mice were evident.

Figure 7:
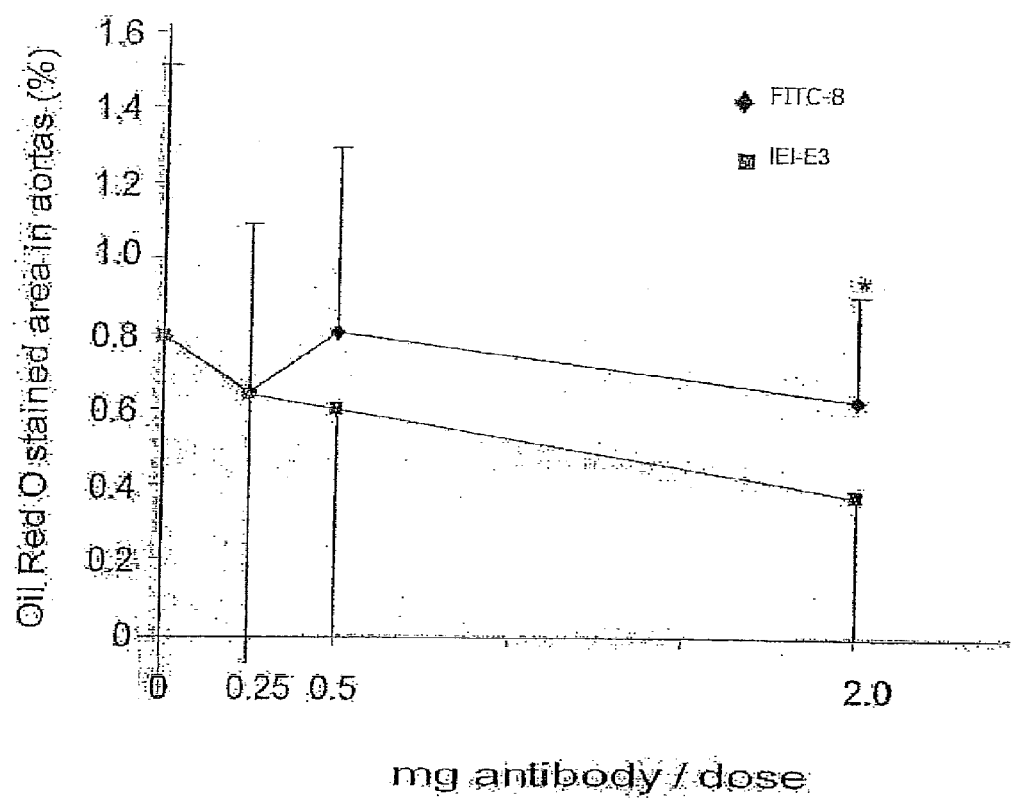
FIG. 7 is a graph of Oil Red O stained area in aortas versus antibody product.

To verify the inhibitory effect of the IEI-E3 antibody on development of atherosclerosis we then performed a dose-response study. The schedule was identical to that of the initial study. In mice treated with IEI-E3 antibodies atherosclerosis was reduced by 2% in the 0.25 mg group (n.s.), by 25% in the 0.5 mg group (n.s.) and by 41% (P=0.02) in the 2.0 mg group as compared to the corresponding FITC antibody-treated groups (FIG. 7).

2. Effect of antibodies on neo-intima formation following mechanical injury of carotid arteries in apo E- mice. Mechanical injury of arteries results in development of fibro-muscular neo-intimal plaque within 3 weeks. This plaque resembles morphologically a fibro-muscular atherosclerotic plaque and has been used as one model for studies of the development of raised lesion. Placing a plastic collar around the carotid artery causes the mechanical injury. Five weeks old apo E- mice are fed a cholesterol-rich diet for 14 weeks. The mice are then given an intraperitoneal injection containing 500 µg of the respective antibody. Control mice are given 500 µg of an irrelevant control antibody or PBS alone. The treatment is repeated after 7 days and the surgical placement of the plastic collar is performed 1 day later. A last injection of antibodies or PBS is given 6 days after surgery and the animals are sacrificed 15 days later. The injured carotid artery is fixed, embedded in paraffin and sectioned. The size of the neo-intimal plaque is measured using computer-based image analysis.

Figure 8:
FIGS. 8a and 8b are graphs of LDL uptake.

3. Effect of antibodies on uptake of oxidized LDL in cultured human macrophages. Uptake of oxidized LDL in arterial macrophages leading to formation of cholesterol-loaded macrophage foam cells is one of the most characteristic features of the atherosclerotic plaque. Several lines of evidence suggest that inhibiting uptake of oxidized LDL in arterial macrophages represent a possible target for treatment of atherosclerosis. To study the effect of antibodies on macrophage uptake of oxidized c are pre-incubated with $^{125}$I-labeled human oxidized LDL for 2 hours. Human macrophages are isolated from blood donor buffy coats by centrifugation in Ficoll hypaque followed by culture in presence of 10% serum for 6 days. The cells are then incubated with medium containing antibody/oxidized LDL complexes for 6 hours, washed and cell-associated radioactivity determined in a gamma-counter. Addition of IEI-E3 antibodies resulted in a five-fold increase in the binding (P=0.001) and uptake (P=0.004) of oxidized LDL compared to FITC-8 into macrophages, but had no effect on binding or uptake of native LDL (FIGS. 8a and 8b).

4. Effect of antibodies on oxidized LDL-dependent cytotoxicity. Oxidized LDL is highly cytotoxic. It is believed that much of the inflammatory activity in atherosclerotic plaques is explained by cell injury caused by oxidized LDL. Inhibition of oxidized LDL cytotoxicity thus represents another possible target for treatment of atherosclerosis. To study the effect of antibodies on oxidized LDL cytotoxicity cultured human arterial smooth muscle cells are exposed to 100 ng/ml of human oxidized LDL in the presence of increasing concentrations of antibodies (0-200 ng/ml) for 48 hours. The rate of cell injury is determined by measuring the release of the enzyme LDH.

The experiment shown discloses an effect for a particular antibody raised against a particular peptide, but it is evident to the one skilled in the art that all other antibodies raised against the peptides disclosed will behave in the same manner.

The antibodies of the present invention are used in pharmaceutical compositions for passive immunization, whereby the pharmaceutical compositions primarily are intended for injection, comprising a solution, suspension, or emulsion of a single antibody or a mixture of antibodies of the invention in a dosage to provide a therapeutically or prophylactically active level in the body treated. The compositions may be provided with commonly used adjuvants to enhance absorption of the antibody or mixture of antibodies. Other routes of administration may be the nasal route by inhaling the antibody/antibody mixture in combination with inhalable excipients.

Such pharmaceutical compositions may contain the active antibody in an amount of 0.5 to 99.5% by weight, or 5 to 90% by weight, or 10 to 90% by weight, or 25 to 80% by weight, or 40 to 90% by weight.

The daily dosage of the antibody, or a booster dosage shall provide for a therapeutically or prophylactically active level in the body treated to reduce or prevent signs and sympthoms of atherosclerosis by way of passive immunization. A dosage of antibody according to the invention may be 1 µg to 1 mg per kg bodyweight, or more.

The antibody composition can be supplemented with other drugs for treating or preventing atherosclerosis or heart-vascular diseases, such as blood pressure lowering drugs, such as beta-receptor blockers, calcium antagonists, diurethics, and other antihypertensive agents.

Figure 9:
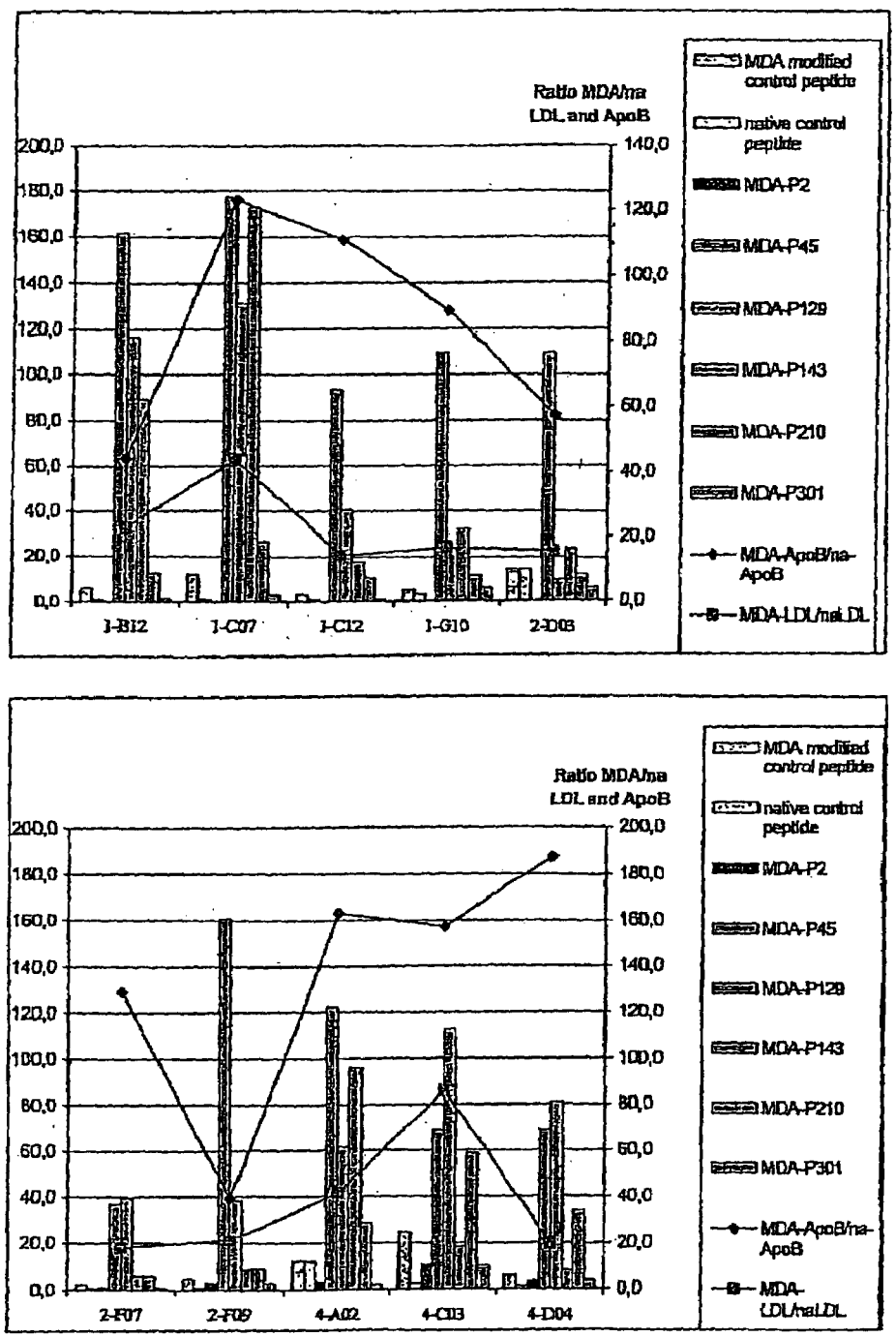
FIG. 9 are graphs of the Ratio MDA/na LDL and ApoB

FIG. 9 shows binding of isolated scFv to MDA modified ApoB100 derived peptides and to a MDA modified control peptide of irrelevant sequence. Also depicted are the ratios between binding of the scFv to MDA modified and native ApoB100 protein and human LDL respectively. Columns appear in the order they are defined from top to bottom in right hand column of the respective subfigure.

REFERENCES

Dimayuga, P., B. Cercek, et al. (2002).
"Inhibitory effect on arterial injury-induced neointimal formation by adoptive B-cell transfer in Rag-1 knockout mice."
*Arteriosclerosis, Thrombosis and Vascular Biology* 22: 644-649.

Jovinge, S., M. Crisby, et al. (1997).
"DNA fragmentation and ultrastructural changes of degenerating cells in atherosclerotic lesions and smooth muscle cells exposed to oxidized LDL in vitro."
*Arteriosclerosis, Thrombosis and Vascular Biology* 17: 2225-2231.

Regnström, J., G. Walldius, et al. (1990).
"Effect of probucol treatment on suspectibility of low density lipoprotein isolated from hypercholesterolemic patients to become oxidativery modified in vitro."
*Atherosclerosis* 82: 43-51.

Steinberg, D., S. Parthasarathy, et al. (1989).
"Beyond cholesterol modifications of low-density lipoprotein that increase its atherogenicity."
*New England Journal of Medicine* 320(14): 915-924.

Zhou, X., G. Paulsson, et al. (1998).
"Hypercholesterolemia is associated with a T heaper (Th) 1/Th2 switch of the autoimmune response in atherosclerotic apo E-knockout Mice."
*Journal of Clinical Investigation* 101: 1717-1725.

The invention claimed is:

1. A method for passive immunization of mammals, preferably humans, wherein a therapeutically effective amount of a isolated human antibody capable of binding to at least one oxidized fragment of apolipoprotein B is administered for treatment of artheroscleosis, wherein the oxidized fragment is (SEQ ID NO: 70)

or an active site thereof, and wherein the antibody comprises a variable heavy region ($V_H$) encoded by (SEQ ID NO: 27) and/or a variable light region (VL) encoded by (SEQ ID NO: 28).

2. The method according to claim 1, wherein the antibody is administered as a pharmaceutical composition, such as a solution, suspension or emulsion.

3. The method according to claim 1, wherein the antibody is administered by injection or nasal administration, including adjuvant and inhalable excipients.

4. The method according to claim 1, wherein the antibody is administered in a composition supplemented with other drugs, including drugs for treating or preventing arthrosclerosis or heart-vascular diseases, such as blood pressure lowering drugs, such as beta-receptor blockers, calcium antagonists, diuretics, and other antihypertensive agents.

5. The method according to claim 1, wherein the antibody is an antibody fragment, such as a scFv or Fab.

* * * * *

UNITED STATES PATENT AND TRADEMARK OFFICE
CERTIFICATE OF CORRECTION

| | | |
|---|---|---|
| PATENT NO. | : 7,601,353 B2 | Page 1 of 1 |
| APPLICATION NO. | : 11/323123 | |
| DATED | : October 13, 2009 | |
| INVENTOR(S) | : Nilsson et al. | |

It is certified that error appears in the above-identified patent and that said Letters Patent is hereby corrected as shown below:

On title page please add:

Related U.S. Application Data

Item (63) Divisional of U.S. Patent Application Serial No. 10/679,032, filed on October 3, 2003, and Provisional application No. 60/421,067, filed on October 25, 2002.

Foreign Application Priority Data

Item (30) October 4, 2002  (SE) ...................0202959-3
   August 27, 2003  (SE) ...................0302314-4

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,353 B2 | Page 1 of 1 |
| APPLICATION NO. | : 11/323123 | |
| DATED | : October 13, 2009 | |
| INVENTOR(S) | : Nilsson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Fifteenth Day of March, 2011

David J. Kappos
*Director of the United States Patent and Trademark Office*